(12) United States Patent
Iwatani et al.

(10) Patent No.: US 10,513,676 B2
(45) Date of Patent: Dec. 24, 2019

(54) MEASUREMENT METHOD FOR UNBOUND BILIRUBIN IN BLOOD SAMPLE

(71) Applicant: National University Corporation Kobe University, Kobe-shi, Hyogo (JP)

(72) Inventors: Sota Iwatani, Kobe (JP); Ichiro Morioka, Kobe (JP); Hajime Nakamura, Kobe (JP); Atsushi Miyawaki, Wako (JP); Akiko Kumagai, Wako (JP)

(73) Assignee: National University Corporation Kobe University, Kobe-shi, Hyogo (JP)

( * ) Notice: Subject to any disclaimer, the term of this patent is extended or adjusted under 35 U.S.C. 154(b) by 117 days.

(21) Appl. No.: 15/563,525

(22) PCT Filed: Mar. 30, 2016

(86) PCT No.: PCT/JP2016/060327
§ 371 (c)(1),
(2) Date: Sep. 29, 2017

(87) PCT Pub. No.: WO2016/159050
PCT Pub. Date: Oct. 6, 2016

(65) Prior Publication Data
US 2018/0087014 A1    Mar. 29, 2018

(30) Foreign Application Priority Data
Mar. 30, 2015    (JP) .................................. 2015-068471

(51) Int. Cl.
  *C12Q 1/00*    (2006.01)
  *C12M 1/34*    (2006.01)
  (Continued)

(52) U.S. Cl.
  CPC .......... *C12M 1/3476* (2013.01); *C12Q 1/005* (2013.01); *C12Q 1/28* (2013.01); *G01N 33/72* (2013.01)

(58) Field of Classification Search
  None
  See application file for complete search history.

(56) References Cited

U.S. PATENT DOCUMENTS 5,376,631 A    12/1994  Stief
5,427,918 A    6/1995   Stief
(Continued)

FOREIGN PATENT DOCUMENTS

JP    2-36200       2/1990
JP    11072497 A    3/1999
(Continued)

OTHER PUBLICATIONS

Kumagai et al., Cell 153: 1602-1611 (2013).*
(Continued)

*Primary Examiner* — Erin M. Bowers
(74) *Attorney, Agent, or Firm* — Knobbe, Martens, Olson & Bear LLP

(57) ABSTRACT

Provided is a measurement method whereby the amount of unbound bilirubin (UB) can be exactly reflected whether a specimen contains a large amount of conjugated bilirubin or not. The measurement method for UB according to the present invention comprises decomposition step (i), decomposition stopping step (ii), contact step (iii) and detection step (iv). In decomposition step (i), a blood sample containing unconjugated bilirubin (iD-Bil) and conjugated bilirubin (D-Bil) is subjected to an oxidative decomposition reaction of UB in iD-Bil and D-Bil. In decomposition stopping step (ii), the oxidative decomposition reaction is stopped to give a decomposition product of the sample. In contact step (iii),
(Continued)

the decomposition product of the sample is contacted with UnaG that is capable of specifically binding to iD-Bil. Separately, an unreacted sample, which is the blood sample not subjected to decomposition step (i), is contacted with UnaG too. In detection step (iv), the fluorescence of UnaG is detected from the decomposition product of the sample and from the unreacted sample. Then, the amount of UB is derived from the difference between the detected values.

15 Claims, 11 Drawing Sheets

Specification includes a Sequence Listing.

(51) Int. Cl.
*C12Q 1/28* (2006.01)
*G01N 33/72* (2006.01)

(56) References Cited

U.S. PATENT DOCUMENTS

| | | | |
|---|---|---|---|
| 5,599,661 | A | 2/1997 | Senba et al. |
| 5,804,405 | A | 9/1998 | Ahlfors |
| 5,869,276 | A | 2/1999 | Kojima et al. |
| 5,935,805 | A | 8/1999 | Ahlfors |
| 7,070,999 | B1 | 4/2006 | Akporiaye et al. |
| 2011/0294997 | A1 | 12/2011 | Geddes |
| 2016/0009771 | A1 | 1/2016 | Miyawaki et al. |

FOREIGN PATENT DOCUMENTS

| | | | |
|---|---|---|---|
| JP | 2001-507790 A | | 6/2001 |
| JP | 2009-139315 A | | 6/2009 |
| WO | WO 98/23965 | * | 6/1998 |
| WO | WO 2014/133158 A1 | | 9/2014 |

OTHER PUBLICATIONS

Department of Pediatrics, Kobe University Graduate School of Medicine, Management in Preterm Infants and Newborns. 1991 Tokyo, Nihon Shoni Iji Shuppan-sha, (in 2 pages, including p. 233), (mentioned in the English translation of the specification at paragraphs [0006] and [0010]).

Kawase, Y. et al. 2006 "Neonatal hyperbilirubinemia"Toru Yamaguchi, Mitsuo Kitahara, Tsuguya Fukui, Omnibus, Today's Therapy, Igaku-Shoin Ltd., Tokyo, pp. 941-942 (mentioned in the English translation of the specification at paragraphs [0007] and [0010]).

Kumagai, et al. 2013 "A bilirubin-inducible fluorescent protein from Eel Muscle" *Cell*; 153: 1602-1611.

Nakamura, et al. 1977 "Microdetermination of unbound bilirubin in icteric newborn sera: An enzymatic method employing peroxidase and glucose oxidase" *Clinica Chimica Acta* 79: 411-417.

Shimabuku, et al. 1982 "Total and unbound bilirubin determination using an automated peroxidase micromethod" *Kobe J. Med. Sci* 28: 91-104.

Supplementary Extended European Search Report in corresponding European Application No. EP 16 77 2931, dated Aug. 29, 2018.

* cited by examiner

Initial ascorbic acid concentration in sample (%)

(a) GOD-POD method

→ Calculate UB from Δt (b) GOD-POD-UnaG method

→ Calculate UB from ΔiDB

SEQUENCE LISTING

```
<160> NUMBER OF SEQ ID NOS: 1

<210> SEQ ID NO 1
<211> LENGTH: 139
<212> TYPE: PRT
<213> ORGANISM: Anguilla japonica

<400> SEQUENCE: 1

Met Val Glu Lys Phe Val Gly Thr Trp Lys Ile Ala Asp Ser His Asn
1               5                  10                  15

Phe Gly Glu Tyr Leu Lys Ala Ile Gly Ala Pro Lys Glu Leu Ser Asp
            20                  25                  30

Gly Gly Asp Ala Thr Thr Pro Thr Leu Tyr Ile Ser Gln Lys Asp Gly
        35                  40                  45

Asp Lys Met Thr Val Lys Ile Glu Asn Gly Pro Pro Thr Phe Leu Asp
    50                  55                  60

Thr Gln Val Lys Phe Lys Leu Gly Glu Glu Phe Asp Glu Phe Pro Ser
65                  70                  75                  80

Asp Arg Arg Lys Gly Val Lys Ser Val Val Asn Leu Val Gly Glu Lys
                85                  90                  95
```

```
Leu Val Tyr Val Gln Lys Trp Asp Gly Lys Glu Thr Thr Tyr Val Arg
            100                 105                 110

Glu Ile Lys Asp Gly Lys Leu Val Val Thr Leu Thr Met Gly Asp Val
            115                 120                 125

Val Ala Val Arg Ser Tyr Arg Arg Ala Thr Glu
    130                 135
```

MEASUREMENT METHOD FOR UNBOUND BILIRUBIN IN BLOOD SAMPLE

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 26801777_1.TXT, the date of creation of the ASCII text file is Sep. 29, 2017, and the size of the ASCII text file is 1.67 KB.

TECHNICAL FIELD

The present invention relates to a method of measuring unbound bilirubin in a blood sample. Specifically, the present invention relates to a method of accurately measuring unbound bilirubin in a blood sample derived from a newborn so as to properly manage jaundice of the newborn. More specifically, the present invention relates to a method of accurately measuring unbound bilirubin in a blood sample derived from a preterm infant so as to reliably predict the development of kernicterus of the preterm infant.

BACKGROUND ART

Kernicterus is a cause of newborn brain disorder. In full-term infants (mature infants), nearly all cases of kernicterus are preventable by early detection and prompt treatment because of the progress in perinatal medical care. As for preterm infants, on the other hand, the number of cases of kernicterus diagnosis has been recently increasing due to, for example, an increase in the survival rate of extremely preterm infants. This trend is a great concern in the field of pediatric and newborn medical care and needs to be addressed urgently.

It is well known that kernicterus is caused by jaundice developed in the newborn period, more specifically, developed by serum bilirubin. Serum bilirubin, which is often called total bilirubin (TB), is a yellow substance that contains unconjugated bilirubin (indirect bilirubin, iDB) and conjugated bilirubin (direct bilirubin, DB). Unconjugated bilirubin has neurotoxicity. A type of unconjugated bilirubin not bound to albumin, namely unbound bilirubin (UB), has a low molecular weight and therefore can easily cross the blood-brain barrier and deposit in the brain. This phenomenon is a significant cause of neurotoxicity.

Techniques for unbound bilirubin measurement have been studied since the 1960s. Among these efforts, inventors of the present invention have reported the glucose oxidase-peroxidase (GOD-POD) method (see Non-patent Document 1: Clin Chim Acta. 1977 Sep. 1; 79(2): 411-7). The inventors have also developed an automatic measurement apparatus (UB-Analyzer manufactured by Arrows) that is based on the GOD-POD method (see Non-patent Document 2: Kobe J Med Sci. 1982 April: 28(2): 91-104). This automatic measurement apparatus is the only clinical apparatus for measuring unbound bilirubin, and is approved by U.S. Food and Drug Administration (FDA) and Japan's Ministry of Health, Labour and Welfare.

The GOD-POD method uses glucose and glucose oxidase to generate hydrogen peroxide and then makes peroxidase act on the hydrogen peroxide to induce oxidative decomposition of bilirubin. In this method, albumin-unbound bilirubin is oxidatively decomposed and readily converted into a colorless substance, whereas albumin-bound bilirubin tends not to be oxidatively decomposed. Therefore, unbound bilirubin concentrations are calculated from the initial rate of the oxidative decomposition. More specifically, unbound bilirubin concentrations are determined by colorimetrically monitoring the decreasing rate of bilirubin pigments.

The criteria for jaundice treatment published from Department of Pediatrics, Kobe University Graduate School of Medicine define the suitable range of concentrations of both serum total bilirubin and unbound bilirubin for indication of phototherapy and exchange transfusion (see Non-patent Document 3: Edited by Department of Pediatrics, Kobe University Graduate School of Medicine, Management in preterm infants and newborns. Tokyo. Nihon Shoni Iji Shuppan-sha, 1991). The wide use of this criteria has greatly contributed to reducing the incidence of kernicterus in mature infants. As for the application to preterm infants, however, some has pointed out that the criteria can lead to overtreatment and therefore the rate of compliance has been decreasing.

There is another set of criteria for jaundice treatment, which exclusively relies on serum total bilirubin concentrations for indication of phototherapy and exchange transfusion (Non-patent Document 4: Yasuhiro Kawase. Neonatal hyperbilirubinemia. Toru Yamaguchi, Mitsuo Kitahara, Tsuguya Fukui, Omnibus, Today's Therapy 2006, Igaku-Shoin Ltd., Tokyo, 2006, pp 941-942).

There is a study that a gene from Japanese eel muscle has been isolated, and the gene codes for a protein that emits green fluorescence. The researchers of this study have found that its gene product, UnaG, specifically binds to unconjugated bilirubin and emits an intense green fluorescence, and that the UnaG-bound bilirubin acts as a fluorescent chromophore (see Non-patent Document 5: Cell. 2013 Jun. 20; 153(7): 1602-11, and Patent Document 1: WO 2014/133158 A).

PRIOR ART DOCUMENTS

Patent Document

Patent Document 1: WO 2014/133158 A

Non-Patent Documents

Non-Patent Document 1: Clinica Chimica Acta, 1977 Sep. 1; 79(2): 411-7.
Non-Patent Document 2: Kobe Journal of Medical Sciences, 1982 April: 28(2): 91-104.
Non-Patent Document 3: Edited by Department of Pediatrics, Kobe University Graduate School of Medicine, Management in preterm infants and newborns. Tokyo, Nihon Shoni Iji Shuppan-sha, 1991
Non-Patent Document 4: Yasuhiro Kawase. Neonatal hyperbilirubinemia. Toru Yamaguchi. Mitsuo Kitahara, Tsuguya Fukui, Omnibus, Today's Therapy 2006, Igaku-Shoin Ltd., Tokyo, 2006, pp 941-942
Non-Patent Document 5: Cell. 2013 Jun. 20; 153(7): 1602-11.

SUMMARY OF THE INVENTION

Problems to be Solved by the Invention

The inventors of the present invention have conducted a nationwide survey to see the incidence of kernicterus in preterm infants. The results have indicated that the annual incidence rate of kernicterus in preterm infants of less than 30 weeks of gestation is 8 to 9 cases/year. However, kernicterus can also develop in preterm infants of not less than 30 weeks and less than 37 weeks of gestation. With those in consideration, the annual incidence rate of kernicterus in preterm infants can probably be higher than the rate indicated by the survey.

Unbound bilirubin levels are usually in correlation with the total bilirubin levels in the same blood. However, such a correlation is not necessarily found in newborns, particularly in preterm infants. According to a survey conducted by the inventors of the present invention, 39% of the preterm infants of less than 30 weeks of gestation in the survey had too high unbound bilirubin (0.8 or higher) for low total bilirubin (lower than 15), accounting for 7 out of 8 cases of low TB kernicterus in the preterm infants. This result, which indicates the presence of not a few cases of high unbound bilirubin levels for low total bilirubin levels, warns that jaundice management exclusively dependent on total bilirubin levels may fail to detect the risk for kernicterus.

It is important to consider the unbound bilirubin levels in jaundice management and there has been a demand for a system that accurately measures unbound bilirubin levels. However, the UB-Analyzer, the only automatic measurement apparatus available, may fail to yield accurate measurement when conjugated bilirubin levels in the specimen are high. When the conjugated bilirubin levels are high, not only unbound bilirubin but also conjugated bilirubin receive oxidative decomposition in the GOD-POD method and consequently the measurement of unbound bilirubin can yield false panic values far from true levels. When such values are yielded, it is very difficult to make a proper clinical decision. This problem is more significant in newborns, particularly in preterm infants, because many infants of such gestational ages have high levels of conjugated bilirubin.

UnaG, a polypeptide described in WO 2014/133158 A (Patent Document 1), specifically binds to unconjugated bilirubin. This phenomenon has led the inventors of the present invention to apply the polypeptide to the GOD-POD measurement system. But this polypeptide, upon contact with albumin-bound bilirubin, makes the albumin be unbound and binds to the bilirubin, making unbound bilirubin unrecognizable from albumin-bound bilirubin. Therefore, the polypeptide cannot be simply applied to the GOD-POD measurement system in which the initial rate of oxidative decomposition of unbound bilirubin is used to determine unbound bilirubin concentrations.

The present invention has been devised based on the above circumstances. An object of the present invention is to provide a method of accurately measuring unbound bilirubin regardless of the levels of conjugated bilirubin.

Means for Solving the Problem

The inventors of the present invention have based their approach on the GOD-POD measurement system. Instead of measuring the initial rate of oxidative decomposition of unbound bilirubin, which has been an essential technique for measurement of unbound bilirubin concentrations, they have adopted termination of the oxidative decomposition. They have calculated the difference in levels of bonded UnaG before and after oxidative decomposition reaction and regarded the difference as unbound bilirubin levels. In other words, they did not use UnaG for specific labelling of the target as in conventional methods. Instead, they have specifically converted the target into a form that is not to be labeled with UnaG. In this way, UnaG has successfully been applied to the GOD-POD measurement system. The present invention contains the following embodiments.

(1)

A method of measuring unbound bilirubin of the present invention includes decomposition step (i), decomposition termination step (ii), contact step (iii), and detection step (iv).

Decomposition step (i) involves subjecting a blood sample containing unconjugated bilirubin and conjugated bilirubin to oxidative decomposition reaction in which unbound bilirubin of the unconjugated bilirubin and the conjugated bilirubin receive the oxidative decomposition reaction.

Decomposition termination step (ii) involves terminating the oxidative decomposition reaction to obtain a decomposed sample.

Contact step (iii) involves bringing the decomposed sample into contact with a polypeptide that has an ability to specifically bind to unconjugated bilirubin and display fluorescence properties and, separately, bringing a non-reacted sample into contact with a polypeptide that has an ability to specifically bind to unconjugated bilirubin and display fluorescence properties. The non-reacted sample is a blood sample which is not subjected to decomposition step (i).

Detection step (iv) involves detecting fluorescence attributable to the polypeptide in each of the decomposed sample and the non-reacted sample and using a difference between the fluorescence attributable to the decomposed sample and the fluorescence attributable to the non-reacted sample to determine a level of unbound bilirubin.

In this embodiment, the blood sample is divided into 2 routes; a route that involves decomposition step (i) and a route that does not involve decomposition step (i). Only along the former route, unbound bilirubin is decomposed into a substance that does not specifically bind to the polypeptide. This means that the unconjugated bilirubin (unbound bilirubin and albumin-bound bilirubin) and the conjugated bilirubin in the blood sample take different paths, as follows: along the route that involves decomposition step (i), albumin-bound bilirubin alone specifically binds to the polypeptide and emits fluorescence, while along the route that does not involve decomposition step (i), unbound bilirubin and albumin-bound bilirubin specifically bind to the polypeptide and emit fluorescence.

This method distinguishes unconjugated bilirubin from conjugated bilirubin and also distinguishes albumin-bound bilirubin from unbound bilirubin contained in the unconjugated bilirubin, enabling accurate measurement of unbound bilirubin regardless of the level of conjugated bilirubin in the specimen. Therefore, this method enables accurate management of newborn jaundice based on measurement of a blood sample collected from a newborn.

This method is based on fluorescence detection and is therefore highly sensitive, enabling measurement even when the amount of the blood sample is very small. Thus, this method enables reduction of the burden of blood collection on a newborn, particularly a preterm infant.

(2)

In the method of measuring unbound bilirubin according to (1), the blood sample may be derived from a preterm infant.

Preterm infants, in particular, have many cases of high unbound bilirubin for low total bilirubin. Therefore, this method enables more effective management of jaundice.

(3)

In the method of measuring unbound bilirubin according to (1) or (2), the blood sample may have a serum total bilirubin concentration of not lower than 8 mg/dL.

In cases of such high concentrations of serum total bilirubin, in particular, conjugated bilirubin levels are often high as well. Because the present invention does not carry out detection of conjugated bilirubin, the method of the present invention is particularly useful in cases of such high conjugated bilirubin levels. More specifically, the method of the present invention enables effective management of newborn jaundice.

(4)

In the method of measuring unbound bilirubin according to any one of (1) to (3), the blood sample may have a conjugated bilirubin concentration of not lower than 1 mg/dL.

Because the present invention does not carry out detection of conjugated bilirubin, the method of the present invention is particularly useful for samples having such high concentrations of conjugated bilirubin.

(5)

In the method of measuring unbound bilirubin according to any one of (1) to (4), the termination of the oxidative decomposition reaction may be carried out by addition of an antioxidant substance.

This aspect allows easy and effective termination of the oxidative decomposition reaction.

(6)

In the method of measuring unbound bilirubin according to (5), the antioxidant substance may be ascorbic acid.

This aspect allows even more easy and effective termination of the oxidative decomposition reaction.

(7)

In the method of measuring unbound bilirubin according to any one of (1) to (6), the termination of the oxidative decomposition reaction may be carried out after a lapse of not shorter than 10 seconds and not longer than 60 seconds from the initiation of the oxidative decomposition reaction in decomposition step (i).

This aspect allows sufficient decomposition of unbound bilirubin in the blood sample and quick measurement of unbound bilirubin.

(8)

In the method of measuring unbound bilirubin according to any one of (5) to (7), the addition of the antioxidant substance may be carried out so as to achieve a concentration of the antioxidant substance of not lower than 0.1 wt % in the reaction system in decomposition termination step (ii).

This aspect allows anti-oxidant action to proceed enough to achieve more reliable termination of the oxidative decomposition reaction.

(9)

In the method of measuring unbound bilirubin according to (8), in a case in which the antioxidant substance is ascorbic acid, the addition of the ascorbic acid may be carried out so as to achieve a concentration of the ascorbic acid of not higher than 32 wt % in the reaction system in decomposition termination step (ii).

This aspect allows easy pH adjustment so as to attain a pH level at which the polypeptide-binding reaction readily occurs in contact step (iii).

(10)

In the method of measuring unbound bilirubin according to any one of (6) to (9), the ascorbic acid may be diluted so as to achieve a concentration of the ascorbic acid of not higher than 0.8 wt % in the reaction system in contact step (iii).

This aspect allows pH adjustment so as to attain a pH level at which the polypeptide-binding reaction readily occurs in the reaction system in contact step (iii).

(11)

In the method of measuring unbound bilirubin according to any one of (1) to (10), a dilution factor of the blood sample in the reaction system in decomposition step (i) may be not smaller than 5 and not greater than 120 in terms of serum.

In this aspect, the concentration of the blood sample subjected to the reaction is relatively high. Therefore, spontaneous bilirubin consumption (such as decomposition due to light exposure and/or due to an unspecified metabolite in the serum) is inhibited to an acceptable degree. Thereby, it is likely that any influence of such spontaneous bilirubin consumption on the reaction of unbound bilirubin decomposition is avoided. Thus, this aspect allows more accurate measurement of unbound bilirubin.

(12)

In the method of measuring unbound bilirubin according to (11), the oxidative decomposition reaction in decomposition step (i) may proceed based on hydrogen peroxide and peroxidase, the hydrogen peroxide being generated from glucose in the presence of glucose oxidase; and the reaction system of the oxidative decomposition reaction may contain the glucose oxidase and the peroxidase each in an amount of not lower than 0.0128 U and not higher than 0.256 U per 1 µL of serum.

The unit, U, referring to the amount of an enzyme in the present specification, is an international unit.

In this aspect, the enzymes are used in concentrations proper for the concentration of the blood sample. Therefore, this aspect allows proper control of the reaction rate in decomposition step (i).

(13)

In the method of measuring unbound bilirubin according to any one of (1) to (12), the blood sample may be a whole blood sample.

This aspect requires no additional step of serum preparation, and, therefore, yields excellent measurement efficiency and enables quick examination of newborn jaundice (which requires urgent attention). In addition, this aspect requires only a small amount of blood and thereby can reduce the burden of blood collection on a newborn, particularly a preterm infant.

(14)

In the method of measuring unbound bilirubin according to (13), the level of the unbound bilirubin determined in detection step (iv) may be obtained after hematocrit correction.

Typically, bilirubin is contained not in the hemocyte component of blood but in the plasma component of blood. Therefore, the level of unbound bilirubin measured in whole blood is lower than that measured in serum or plasma. Hematocrit correction, when carried out here, enables accurate measurement of unbound bilirubin in whole blood.

(15)

A unit for preparing an unbound-bilirubin measurement sample of the present invention has an incubator, a reagent-solution inlet, a blank-reagent-solution inlet, a timer, terminating-agent inlets, and mixers.

The incubator has a reaction-vessel housing and a control-vessel housing.

The reagent-solution inlet is operative to add a reagent solution into a reaction vessel in the reaction-vessel housing.

The reagent solution is a reagent solution for oxidative decomposition of unbound bilirubin.

The blank-reagent-solution inlet is operative to add a blank-reagent solution into a control vessel in the control-vessel housing.

The timer is operative to be actuated in response to the movement of the reagent-solution inlet and the blank-reagent-solution inlet.

The terminating-agent inlets are controlled to be actuated based on the measurement time with the timer. Each of the terminating-agent inlets is operative to add an oxidative-decomposition terminating agent into either the reaction vessel or the control vessel.

Each of the mixers is operative to mix either the content of the reaction vessel or the content of the control vessel.

This embodiment makes decomposition step (i) and decomposition termination step (ii) in the method of measuring unbound bilirubin according to any one of (1) to (14) reduced to a routine, and enables easy and accurate preparation of an unbound-bilirubin measurement sample that is to be subjected to contact step (iii).

(16)

An unbound-bilirubin measurement apparatus of the present invention has the unit for preparing an unbound-bilirubin measurement sample as described in (15), a fluorescence measurement part, an arithmetic processor, and an output part.

The fluorescence measurement part is operative to measure fluorescence in fluorescence-measurement samples. Each of the fluorescence-measurement samples is derived from either a content of the reaction vessel or a content of the control vessel after the addition of the oxidative-decomposition terminating agent and after addition of a polypeptide. The polypeptide has fluorescence properties.

The arithmetic processor is operative to determine a level of unbound bilirubin using at least a difference between a level of fluorescence attributable to the content of the reaction vessel and a level of fluorescence attributable to the content of the control vessel.

The output part is operative to display a resulting level of unbound bilirubin.

This embodiment enables easy and accurate implementation of the method of measuring unbound bilirubin according to any one of (1) to (14).

(17)

The unbound-bilirubin measurement apparatus according to (16) may further have an aliquoting part and an inlet.

The aliquoting part is operative to aliquot and transfer a certain amount of the content of the reaction vessel and a certain amount of the content of the control vessel into a measurement vessel after the addition of the oxidative-decomposition terminating agent.

The inlet is operative to add a liquid containing the polypeptide having fluorescence properties into the measurement vessel.

This embodiment makes the preparation of the fluorescence-measurement samples reduced to a routine, and enables easy and accurate implementation of the method of measuring unbound bilirubin according to any one of (1) to (14).

(18)

An unbound-bilirubin measurement kit of the present invention contains at least: oxidoreductase for oxidatively decomposing unbound bilirubin; an oxidative-decomposition terminating agent for terminating the oxidative decomposition; and a polypeptide having an ability to specifically bind to unconjugated bilirubin and display fluorescence properties.

This embodiment makes it possible to carry out the method of measuring unbound bilirubin according to any one of (1) to (14).

(19)

The unbound-bilirubin measurement kit according to (18) may further contain glucose and glucose oxidase.

This aspect allows easy control of the timing of the initiation of unbound bilirubin decomposition and easy control of the decomposition rate.

(20)

In the unbound-bilirubin measurement kit according to (18) or (19), the oxidoreductase may be peroxidase.

This aspect enables effective oxidative decomposition of unbound bilirubin.

(21)

In the unbound-bilirubin measurement kit according to any one of (18) to (20), the oxidative-decomposition terminating agent may be an antioxidant substance.

This aspect enables easy and effective termination of the oxidative decomposition reaction.

(22)

In the unbound-bilirubin measurement kit according to (21), the antioxidant substance may be ascorbic acid.

This aspect enables easy and effective termination of the oxidative decomposition reaction.

Advantages of the Invention

The present invention enables accurate measurement of unbound bilirubin regardless of the level of conjugated bilirubin in the specimen. Therefore, this method enables accurate management of newborn jaundice, for example.

EMBODIMENTS OF THE INVENTION

[1. Principle of Measurement]

Figure 1:
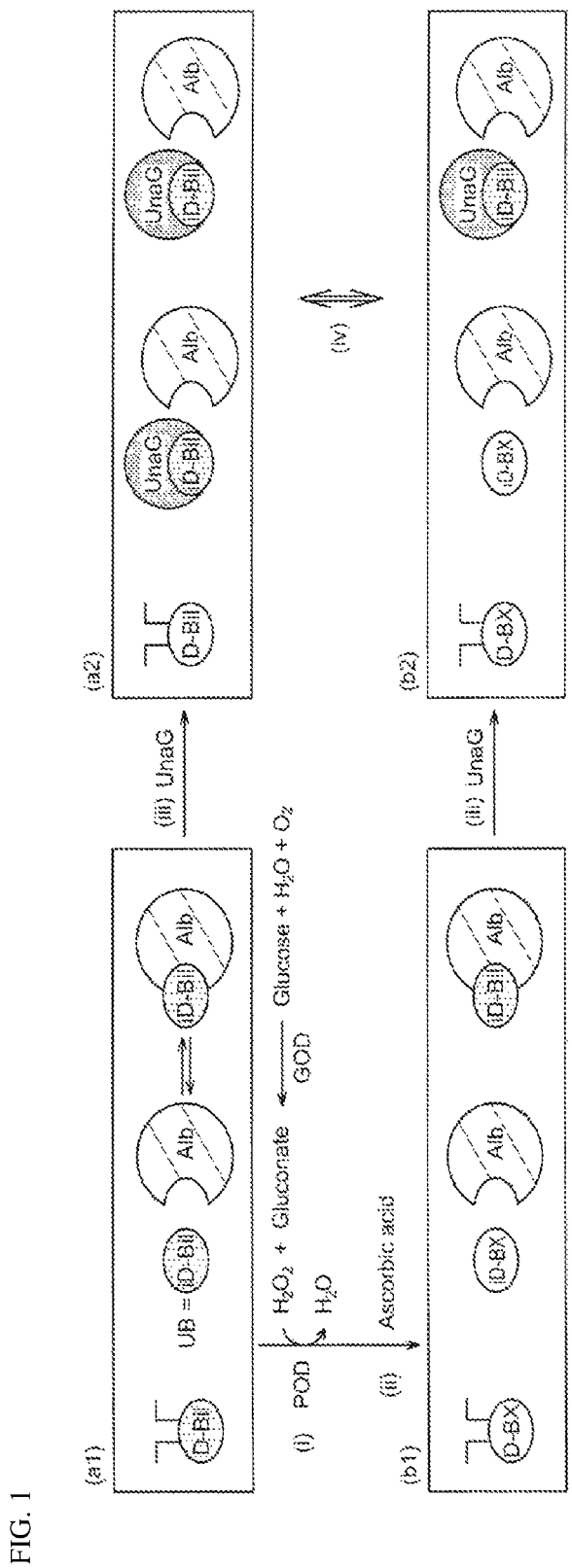
FIG. 1 schematically shows the principle of measurement in an embodiment of the present invention.

FIG. 1 schematically shows the principle of measurement in an embodiment of the present invention. In FIG. 1, D-Bil represents conjugated bilirubin; iD-Bil represents unconjugated bilirubin; Alb represents albumin; iD-Bil free from albumin (Alb) represents unbound bilirubin (UB); D-BX represents a decomposition product of conjugated bilirubin; iD-BX represents a decomposition product of unbound bilirubin; and UnaG represents an example of a fluorescent polypeptide that specifically binds to conjugated bilirubin (iD-Bil).

[1-1. Measurement Sample]

In FIG. 1, (a1) represents a blood sample (non-reacted sample). As long as the blood sample contains conjugated bilirubin (D-Bil) and unbound bilirubin (UB) that is contained in unconjugated bilirubin (iD-Bil), the blood sample may be either a blood sample derived from either a human or a non-human living organism or an artificial blood sample containing conjugated bilirubin (D-Bil) and/or unbound bilirubin (UB) in a known concentration.

From the viewpoint of clinical significance, it is preferable that blood sample (a1) be derived from a human infant, particularly a human newborn infant. Blood sample (a1) contains total bilirubin, more specifically, conjugated bilirubin (D-Bil) and unconjugated bilirubin (iD-Bil). Most of the unconjugated bilirubin (iD-Bil) is in a form of albumin-(Alb)-bound bilirubin, and the rest is free from albumin (Alb) and exists as unbound bilirubin (UB), which is a neurotoxin. More specifically, blood sample (a1) may be whole blood, plasma, or serum, and the blood sample is appropriately obtained and prepared by those skilled in the art. In the preparation, a treatment such as treatment to obtain plasma, treatment to obtain serum, or dilution treatment is carried out.

A newborn generally refers to an infant not less than 0 day and less than 28 days after birth. Here, the day of birth is counted as day 0. In newborns, there are many cases of too high unbound bilirubin (UB) for a typical correlation between total bilirubin and unbound bilirubin (UB) and, therefore, accurate measurement of unbound bilirubin (UB) is highly required. Thus, it is preferable that the blood sample be derived from a newborn who has a factor that can raise the unbound bilirubin (UB) concentration, such as a newborn having hypoalbuminemia, receiving drug therapy, or having an infectious disease. It is particularly preferable that the blood sample be derived from a preterm infant who is highly likely to have such a factor. The preterm infant generally refers to a newborn of less than 37 weeks of gestation, and is more preferably a newborn of less than 30 weeks of gestation.

An infant of not less than 28 days after birth can have such a factor, and therefore the present invention may be applied to an infant of not less than 28 days after birth.

The measurement method of the present invention is not affected by conjugated bilirubin (D-Bil) concentrations in the blood sample. Therefore, the present invention is particularly useful in cases in which the blood sample is likely to contain conjugated bilirubin (D-Bil) in a high concentration, for example, in cases in which the total bilirubin concentration in the blood sample is not lower than 5 mg/dL, preferably not lower than 8 mg/dL, particularly preferably not lower than 20 mg/dL. The upper limit to the total bilirubin concentration that is measurable in the present invention is not particularly limited, but may be, for example, up to 40 mg/dL, preferably up to 30 mg/dL.

More specifically, the present invention is particularly useful in cases in which the conjugated bilirubin (D-Bil) concentration is not lower than 0.5 mg/mL, preferably not lower than 1 mg/mL, further preferably not lower than 2.5 mg/mL, or in terms of the ratio (conjugated bilirubin/(total bilirubin) of the conjugated bilirubin (D-Bil) concentration to the total bilirubin concentration, preferably not lower than 10%, more preferably not lower than 20%. The inventors of the present invention have confirmed that in the conventional method of measuring unbound bilirubin (UB) according to the GOD-POD method and in the case in which the (conjugated bilirubin)/(total bilirubin) ratio of the specimen is within the above range, unbound bilirubin (UB) tends to be measured higher than the level that is typically expected from total bilirubin.

In addition, the measurement method of the present invention is not affected by whether the blood donor has received phototherapy. Therefore, bilirubin in the blood sample of the present invention may be soluble in fat or may have been converted into a water-soluble structural isomer (cyclobilirubin) by the action of light.

[1-2. Decomposition Step]

As shown in FIG. 1, blood sample (a1) is subjected to decomposition step (i). In decomposition step (i), conjugated bilirubin (D-Bil) and unbound bilirubin (UB) in blood sample (a1) receive oxidative decomposition. The decomposition reaction in this step is not particularly limited provided that the decomposition reaction at least converts unbound bilirubin (UB) into a substance that does not bind to a fluorescent polypeptide used in step (iii) below and that the decomposition reaction does not change the ability of albumin-(Alb)-bound bilirubin to bind to the fluorescent polypeptide.

The oxidative decomposition may be made proceed by using oxidoreductase and transferring hydrogen of bilirubin to a hydrogen acceptor, which is a peroxide. It is preferable to use peroxidase as the oxidoreductase and hydrogen peroxide as the peroxide, as shown in FIG. 1.

The hydrogen peroxide may be generated in the reaction system in decomposition step (i). It is more preferable that the hydrogen peroxide be generated together with a gluconate from glucose, water, and oxygen in the presence of GOD (glucose oxidase), as shown in FIG. 1. The peroxidase is made act on the resulting hydrogen peroxide, causing oxidative decomposition of bilirubin. The rate of the decomposition depends on the peroxidase. In this embodiment, by controlling the timing of addition of the peroxidase and the concentration of the peroxidase, the timing of the initiation of unbound bilirubin (UB) decomposition and the decomposition rate of unbound bilirubin (UB) may be easily controlled. Therefore, this embodiment is preferable. Although this embodiment adopts a configuration in which hydrogen peroxide is generated in the reaction system in decomposition step (i), the present invention also contains an embodiment in which neither glucose nor glucose oxidase is used and hydrogen peroxide is added as a reagent from outside the system.

As shown in FIG. 1, both of unbound bilirubin (UB) and conjugated bilirubin (D-Bil) in blood sample (a1) receive oxidative decomposition in decomposition step (i). By the oxidative decomposition, unbound bilirubin (UB) and conjugated bilirubin (D-Bil) are converted into a colorless unbound-bilirubin decomposition product (iD-BX) and a colorless conjugated-bilirubin decomposition product (D-BX), respectively.

[1-3. Decomposition Termination Step]

In blood sample (a1), unbound bilirubin (UB) and albumin-(Alb)-bound bilirubin are in equilibrium. If release of unbound bilirubin (UB) lasts too long, the decomposition reaction of unbound bilirubin (UB) may still occur in contact step (iii) described below. This phenomenon is avoided by carrying out decomposition termination step (ii), which yields decomposed sample (b1).

In decomposition termination step (ii), any method of terminating the reaction in decomposition step (i) may be employed. More specifically, an oxidative-decomposition terminating agent may be added to the reaction system that constitutes decomposition step (i).

For example, from the viewpoint of easy and effective termination of the decomposition reaction, an antioxidant substance may be added as the oxidative-decomposition terminating agent. Examples of the antioxidant substance include glutathione. N-acetylcysteine, ascorbic acid (vitamin C), α-tocopherol (vitamin E), butylated hydroxyanisole, catechin, quercetin, uric acid, and flavonoid. Ascorbic acid is preferable in terms of cost and is also excellent in availability, handleability (high water solubility), and the effect of terminating decomposition, for example. Therefore, by using ascorbic acid as shown in FIG. 1, termination of the decomposition reaction may be carried out more easily and more effectively.

Other examples of the oxidative-decomposition terminating agent include ferrocyanide ion; EDTA-iron complex; a ferrocyanide and albumin; a cationic surfactant and/or an amphoteric surfactant; an amphoteric surfactant and a ferrocyanide; a polyoxyethylene alkyl ether and ferrocyanide ion; an iron complex and a steroid compound; a polyoxyethylene alkyl phenyl ether condensate; a saturated or unsaturated fatty acid containing not less than 8 and not more than 24 carbon atoms (more specifically, octanoic acid, decanoic acid, lauric acid, myristic acid, palmitic acid, stearic acid, oleic acid, linoleic acid, linolenic acid, eicosatrienoic acid, arachidonic acid, icosanoic acid, eicosatetraenoic acid, eicosapentaenoic acid, docosanoic acid, docosahexaenoic acid, tetradocosanoic acid, and tetracosapentaenoic acid); or the like.

In the case in which the blood donor is receiving vitamin C therapy via infusion or the like, the blood sample may be treated with ascorbate oxidase prior to decomposition step (i) so as to avoid the decomposition step from being affected by the ascorbic acid contained in the blood sample and thereby achieve accurate measurement. Alternatively in this case, an oxidative-decomposition terminating agent except for ascorbic acid may be used for effective termination of the decomposition.

[1-4. Contact Step]

In contact step (iii), each of non-reacted sample (a1) not subjected to decomposition step (i) and decomposed sample (b1) subjected to decomposition step (i) is brought into contact with a polypeptide (fluorescent polypeptide) that has an ability to specifically bind to unconjugated bilirubin (iD-Bil) and display fluorescence properties. In FIG. 1, a fluorescent polypeptide named UnaG is used. By this process, non-reacted sample (a1) yields fluoresceinated non-reacted sample (a2) and decomposed sample (b1) yields fluoresceinated decomposed sample (b2).

The fluorescent polypeptide used in contact step (iii) has at least 2 properties described below. The first property is that the fluorescent polypeptide specifically binds to unconjugated bilirubin (iD-Bil) and does not bind to conjugated bilirubin (D-Bil), the decomposition product (D-BX) thereof, or a decomposition product (iD-BX) of unbound bilirubin (UB). The second property is as follows: a holo form of the fluorescent polypeptide, namely the fluorescent polypeptide that is specifically bound to unconjugated bilirubin (iD-Bil), emits fluorescence with a certain wavelength upon irradiated with excitation light; and an apo form of the fluorescent polypeptide, namely the fluorescent polypeptide in the absence of unconjugated bilirubin (iD-Bil), emits no fluorescence upon irradiated with the same excitation light. The intensity of the fluorescence depends on the concentration of unconjugated bilirubin (iD-Bil).

The third property of the fluorescent polypeptide is that upon contact with albumin-(Alb)-bound bilirubin, the fluorescent polypeptide may cut the binding between albumin (Alb) and unconjugated bilirubin (iD-Bil) and bind to the unconjugated bilirubin (iD-Bil).

The fluorescent polypeptide UnaG illustrated in the embodiment shown in FIG. 1 has all of these 3 properties. Therefore, in fluoresceinated non-reacted sample (a2), UnaG binds to unconjugated bilirubin (iD-Bil) regardless of whether the unconjugated bilirubin (iD-Bil) is bound to albumin (Alb) or not, in other words, UnaG binds to both unbound bilirubin (UB) and albumin-(Alb)-bound bilirubin and emits fluorescence with an intensity corresponding to the amount of the bound fluorescent polypeptide. In fluoresceinated decomposed sample (b2), UnaG binds to albumin-(Alb)-bound bilirubin alone.

The fluorescent polypeptide used in contact step (iii) is not particularly limited provided that it has all of these 3 properties. Specific examples of the fluorescent polypeptide may include polypeptides essentially composed of UnaG, such as the following (A) to (D).
(A) A fluorescent polypeptide (UnaG) having an amino acid sequence represented by SEQ ID NO: 1.
(B) A fluorescent polypeptide having the amino acid sequence represented by SEQ ID NO: 1 including substitution, deletion, insertion, and/or addition of not lower than 1 and not higher than 21 amino acids. For the properties described above to be suitably satisfied, it is preferable that the number of substituted, deleted, inserted, and/or added amino acids be from not lower than 1 to not higher than 21, higher preferably from not lower than 1 to not higher than 14, further preferably from not lower than 1 to not higher than 7, particularly preferably from not lower than 1 to not higher than 5 or from not lower than 1 to not higher than 6.
(C) A fluorescent polypeptide having a sequence identity to the amino acid sequence represented by SEQ ID NO: 1 of not lower than 85%. For the properties described above to be suitably satisfied, it is preferable that the sequence identity be not lower than 90%, more preferably not lower than 95%, particularly preferably not lower than 96%, not lower than 97%, not lower than 98%, or not lower than 99%.
(D) A fluorescent polypeptide having an amino acid sequence encoded by a polynucleotide that hybridizes under stringent conditions with a polynucleotide having a sequence complementary to that of a polynucleotide coding for the fluorescent polypeptide described above in (A). Examples of the stringent conditions include the conditions described in a reference [Molecular cloning—a Laboratory manual 2nd edition (Sambrook et al., 1989)]. Specific examples of the stringent conditions include a set of conditions in which the polynucleotide is incubated with a probe for hybridization in a solution containing 6×SSC (composition of 1×SSC is 0.15 M sodium chloride, 0.015 M sodium citrate, pH 7.0), 0.5% SDS, 5×Denhardt's solution, and 100 mg/mL herring sperm DNA at 65° C. for a duration of not shorter than 8 hours and not longer than 16 hours; and those in which after hybridization under this set of conditions, the resultant is rinsed at 65° C. in a solution containing a salt at a concentration of about 0.1 M or lower, preferably in 0.2×SSC or any other solution having a similar ionic strength. It is preferable that the polynucleotide have a sequence identity to the nucleotide sequence of the polynucleotide coding for the fluorescent polypeptide described in (A) of not lower than 85%, more preferably not lower than 90%, further preferably not lower than 95%, not lower than 96%, not lower than 97%, not lower than 98%, or not lower than 99%.

The fluorescent polypeptide may be any polypeptide made of amino acid residues linked by peptide bonds, but is not limited to such a polypeptide. Alternatively, the fluorescent polypeptide may have a structure other than a polypeptide structure. The structure other than a polypeptide structure is not particularly limited and examples thereof include sugar chains and isoprenoid groups. Because the properties described above need to be satisfied, the fluorescent polypeptide needs to have a structure that forms a binding site to bind to unconjugated bilirubin (iD-Bil).

The fluorescent polypeptide may be isolated from a natural source or may be obtained artificially. More specifically, the fluorescent polypeptide may be purified from a natural source, may be chemically synthesized, or may be a translation product derived from a prokaryotic host or a eukaryotic host (such as bacterial cells, yeast cells, cells of higher-plants, insect cells, and mammal cells) by a recombinant technique. The artificially obtained fluorescent polypeptide may have the protein structure of any one of (A) to (D) described above, for example, that has an affinity tag added thereto for the purpose of purification or the like. Examples of the fluorescent polypeptide include a fluorescent polypeptide derived from eel, more specifically a fluorescent polypeptide derived from Japanese eel.

The fluorescence emitted by the fluorescent polypeptide may have a maximum excitation wavelength of not smaller than 480 nm and not greater than 520 nm, or not smaller than 490 nm and not greater than 510 nm, or not smaller than 494 nm and not greater than 504 nm, and a maximum fluorescence wavelength of green fluorescence of not smaller than 507 nm and not greater than 547 nm, or not smaller than 517 nm and not greater than 537 nm, or not smaller than 522 nm and not greater than 532 nm. The fluorescence emitted by UnaG, in particular, may have the following main properties: a maximum excitation wavelength of not smaller than 498 nm and not greater than 499 nm; a maximum fluorescence wavelength of not smaller than 525 nm and not greater than 530 nm; a molar absorption coefficient of not lower than 50,000 $M^{-1}$ $cm^{-1}$ and not higher than 78,000 $M^{-1}$ $cm^{-1}$; a quantum yield of not lower than 50% and not higher than 54%; and a fluorescence lifetime of 2.2 nanoseconds.

The specific fluorescent polypeptide described above, in particular UnaG, binds to unconjugated bilirubin (iD-Bil) immediately upon contact and has intense fluorescence activity even when the amount of unconjugated bilirubin (iD-Bil) is small. Therefore, the specific fluorescent polypeptide described above, in particular UnaG, enables highly sensitive and accurate measurement of a trace amount of fluoresceinated non-reacted sample (a2) or fluoresceinated decomposed sample (b2). More specifically, there is no problem when the initial amount of blood sample (a1) is very small or when it is necessary to simultaneously prepare the 2 routes, namely, fluoresceinated non-reacted sample (a2) and fluoresceinated decomposed sample (b2) in a single measurement. This is a feature that greatly contributes to the usefulness of the fluorescent polypeptide as a routine examination of newborn jaundice.

[1-5. Detection Step]

In detection step (iv), each of fluoresceinated non-reacted sample (a2) and fluoresceinated decomposed sample (b2) is irradiated with excitation light, and the resulting fluorescence having a certain wavelength is detected. Fluoresceinated non-reacted sample (a2) emits fluorescence attributable to the binding of unbound bilirubin (UB) to the fluorescent polypeptide (UnaG). Fluoresceinated decomposed sample (b2) emits no fluorescence because the unbound-bilirubin decomposition product (iD-BX) does not bind to the fluorescent polypeptide (UnaG).

The intensity of the fluorescence emitted from a holo form of the fluorescent polypeptide correlates with the amount of the bonded fluorescent polypeptide. Therefore, by measuring the intensity of the fluorescence emitted from fluoresceinated non-reacted sample (a2) and fluoresceinated decomposed sample (b2) and calculating the difference between these 2 values, the amount of unbound bilirubin (UB) is determined.

[1-6. Diagnosis]

The resulting amount of unbound bilirubin (UB) thus measured may be used for jaundice management of the donor of the blood sample. For example, this amount may be used to predict the possibility of the development of kernicterus and determine the indication for a therapy such as phototherapy, exchange transfusion, plasmapheresis, or therapeutic infusions of γ-globulin and, furthermore, may be used to evaluate the therapeutic effect at the time of post-therapy follow-ups. Cut-off levels for use as a diagnostic criterion may be derived from accumulated cases. Separate cut-off levels may be set for infants of less than 30 weeks of gestation and infants of not less than 30 weeks of gestation, or for infants with a birth weight of lower than 1500 g and infants with a birth weight of not lower than 1500 g.

The present invention involves measuring the unbound bilirubin levels according to the principle of measurement described above. However, the measurement results of the present invention may be combined as appropriate with measurement results obtained by at least one of the following methods: a method of measuring total bilirubin; a method of measuring conjugated bilirubin; and other methods of measuring unbound bilirubin (the GOD-POD method, in other words, a method of determining the unbound bilirubin levels from the rate at which the total bilirubin levels decrease due to decomposition of unbound bilirubin).

[2. Protocol and Conditions]

Figure 2:
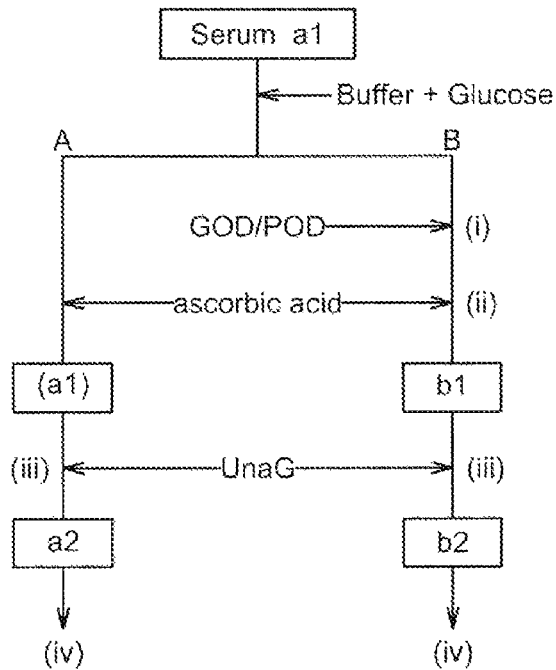
FIG. 2 illustrates a protocol for a measurement method of the present invention.

FIG. 2 illustrates a protocol for the measurement method of the present invention. Conditions in the steps that are contained in the protocol are described below in more detail.

In the illustration shown in FIG. 2, serum is used as blood sample (a1). In the case in which the blood sample is serum as shown in FIG. 2, the initial amount of the blood sample may be, for example, not lower than 0.5 μl and not higher than 25 μl (or if the blood sample is not serum but whole blood or the like, the same range applies to the initial amount of the blood sample in terms of serum). The method of the present invention enables measurement of the blood sample in cases in which the dilution factor in contact step (iii) is great, in other words, enables measurement of a trace amount of the blood sample. Thus, the amount of the blood sample (in terms of serum) may be very small, for example, smaller than 1 μm. In view of handleability of dilution procedure in each step, however, it is preferable that the amount of the blood sample (in terms of serum) be, for example, not smaller than 0.8 μl and not greater than 2 μl, particularly preferably at least 1 μl.

[2-1. Conditions in Decomposition Step (i)]

Blood sample (a1) is mixed with the buffer (Buffer) for dilution (first dilution). In this embodiment, the buffer (Buffer) contains glucose so as to generate hydrogen peroxide in the reaction system. The buffer may be PBS buffer (phosphate-buffered saline), acetate buffer, or Tris buffer, for example.

By this dilution with the buffer, blood sample (a1) is diluted, for example, not smaller than 1.5 times or not smaller than 1.8 times (volume basis) in terms of serum (in other words, the dilution factor is based on the concentration of serum in the blood sample). For easy preparation, it is preferable that the dilution factor be not smaller than this lower limit. The upper limit to the dilution factor is not particularly limited. However, in consideration of a change in the equilibrium between bilirubin and albumin due to an increase in the dilution factor and in order to avoid decomposition and spontaneous consumption of bilirubin due to light exposure and/or due to an unspecified metabolite in the serum, it is preferable that blood sample (a1) be not diluted too thin. From these viewpoints, the dilution factor of blood sample (a1) in terms of serum may be, for example, not greater than 55, not greater than 2.5, or not greater than 2.2 (volume basis).

The concentration of glucose in the buffer (Buffer) is determined, as appropriate, in consideration of the dilution factor described above and the proper amount of glucose as a substrate for glucose oxidase (GOD) in the reaction system in decomposition step (i). For example, the concentration of glucose in the buffer (Buffer) may be determined so that the amount of glucose per 1 U of glucose oxidase in the reaction system in decomposition step (i) is not lower than 0.3 mg and not higher than 1 mg, preferably not lower than 0.3 mg and not higher than 0.5 mg and is, for example, 0.312 mg. Thus, the concentration of glucose in the buffer may be not lower than 1 mg/mL and not higher than 100 mg/mL, preferably not lower than 1 mg/mL and not higher than 10 mg/mL and may be, for example, 1 mg/mL.

A portion of the blood sample after the dilution (or the diluted blood sample) is used for route A, and another portion of the diluted blood sample is used for route B.

To the diluted blood sample for route B in this embodiment, a buffer (GOD/POD buffer) containing glucose oxidase (GOD) and peroxidase (POD) is added. The resultant is used as the reaction system in decomposition step (i) provided that proper temperature conditions are established. The buffer used in the GOD/POD buffer may be selected, as appropriate, from the above examples of the buffer used for first dilution.

In the reaction system in decomposition step (i), blood sample (a1) is further diluted with the GOD/POD buffer. The dilution factor of blood sample (a1) in terms of serum in the reaction system in decomposition step (i) may be, for example, not greater than 120, preferably not greater than 70, and may be, for example, 52.5. For avoiding spontaneous bilirubin consumption, it is preferable that the dilution factor be not greater than this upper limit. The lower limit to the dilution factor is not particularly limited, but in view of handleability of dilution procedure, for example, the lower limit to the dilution factor may be 5, for example.

The amounts of GOD and POD in the GOD/POD buffer are determined, as appropriate, in consideration of the dilution factor described above and the proper amounts of GOD and POD each as an enzyme in the reaction system in decomposition step (i). The amount of GOD is determined so that 1 µl (in terms of serum) of blood sample (a1) contains, for example, not lower than 0.0128 U and not higher than 0.256 U, preferably not lower than 0.05 U and not higher than 0.2 U, and, for example, 0.16 U of GOD. The amount of POD is determined so that 1 µl (in terms of serum) of blood sample (a1) contains, for example, not lower than 0.0128 U and not higher than 0.256 U, preferably not lower than 0.05 U and not higher than 0.2 U. and, for example, 0.16 U of POD. In the case in which the amounts of GOD and POD are within these ranges, decomposition of unbound bilirubin can proceed at a proper rate, more specifically, at a rate that is neither too slow nor too fast. The amount of GOD may be the same as the amount of POD.

The reaction temperature in decomposition step (i) is, for example, not lower than 28° C. and not higher than 38° C. and, for example, 37° C. The reaction in decomposition step (i) completes rapidly, and therefore it is preferable that the temperatures of both the diluted blood sample and the GOD/POD buffer be adjusted to the temperature described above by warming or the like immediately before the reaction system is established.

The diluted blood sample for route A is subjected to the same procedure except for the addition of GOD or POD. More specifically, the diluted blood sample receives addition of a buffer containing neither GOD nor POD and is placed under the same temperature conditions.

[2-2. Conditions in Decomposition Termination Step (ii)]

The reaction in decomposition step (i) is terminated by the addition of a buffer containing ascorbic acid. The buffer to which ascorbic acid is added may be selected, as appropriate, from the above examples of the buffer used for first dilution. Because route A and route B are subjected to the same conditions except for the presence of decomposition reaction (i), route A and route B both receive addition of the buffer containing ascorbic acid in the same manner. Route A has not undergone decomposition reaction (i) and, therefore, the bilirubin composition in the sample is the same as that in the initial blood sample (a1) (see FIG. 1). In other words, this sample remains non-reacted. Therefore, this sample is called non-reacted sample (a1). Route B has undergone decomposition reaction (i) and, therefore, the bilirubin composition in the sample has changed. Therefore, this sample is called decomposed sample (b1) (see FIG. 1).

It is desirable that the timing to carry out decomposition termination step (ii) be the time point of the completion of decomposition of unbound bilirubin (UB) that has been free in blood sample (a1) since the initiation of the reaction in decomposition step (i). The duration after the initiation of the reaction in decomposition step (i) and before the initiation of decomposition termination step (ii) may be determined in consideration of, for example, the dilution factor of the blood sample in the reaction system in decomposition step (i).

For example, the duration may be determined as follows: in an assumed system where the level of conjugated bilirubin (D-Bil) is normal and thereby the degree of a decrease of total bilirubin may be regarded as equivalent to the degree of a decrease of unconjugated bilirubin, the duration may be regarded as equivalent to the time period that is required for the concentration of total bilirubin to decrease about 20% (more specifically, not less than 18% and not more than 25%) from its initial concentration. Here, by the time at which thorough mixing achieves homogeneity of the reaction system in decomposition step (i), the concentration of total bilirubin decreases about 5%. Based on this phenomenon, the duration may be regarded, more specifically, as equivalent to the time period for the concentration of total bilirubin to decrease from 95% to 76% of the initial concentration of total bilirubin (regarded as 100%). Even more specifically, the duration may be, for example, not shorter than 10 seconds and not longer than 60 seconds, preferably not shorter than 15 seconds and not longer than 35 seconds, more preferably not shorter than 15 seconds and not longer than 25 seconds, and may be, for example, 20 seconds, after the initiation of the reaction in decomposition step (i). It is preferable that the timing of decomposition termination be not earlier than the earliest limit of this range for reliable decomposition of unbound bilirubin that should be decomposed. It is preferable that the timing of decomposition termination be not later than the latest limit of this range for excellent reproducibility of the measurement.

The reaction temperature in decomposition termination step (ii) may be, for example, not lower than 20° C. and not higher than 38° C. and may be, for example, 37° C. The amount of ascorbic acid for successfully terminating decomposition may be not lower than 0.0015 mg per 1 U of POD used in decomposition step (i). The amount of ascorbic acid may be increased for quickly and reliably terminating decomposition, and in this case, the amount of ascorbic acid may be, for example, not lower than 0.015 mg and not higher than 120 mg, preferably not lower than 1.5 mg and not higher than 50 mg, and may be, for example, 1.73 mg, per 1 U of POD. More specifically, the concentration of ascorbic acid in the buffer containing ascorbic acid and the amount of the buffer containing ascorbic acid to be added may be determined so that the final concentration of ascorbic acid after the addition to the reaction liquid in decomposition step (i) is, for example, not lower than 0.1 wt % and not higher than 32 wt %/o, preferably not lower than 0.2 wt % and not higher than 10 wt %, and is, for example, 0.35 wt %. The dilution factor of the blood sample after the addition of the buffer containing ascorbic acid may be not smaller than 5 and not greater than 120, preferably not smaller than 10 and not greater than 100, and may be, for example, 80, in terms of serum.

It is preferable that the final concentration of ascorbic acid be not lower than the lower limit for reliable termination of decomposition of unbound bilirubin (UB). It is preferable that the concentration of ascorbic acid be not higher than the upper limit because when the concentration of ascorbic acid is not higher than the upper limit, the pH does not become too acidic and therefore the pH is easily made back to a neutral pH that does not affect the binding with the fluorescent polypeptide in the subsequent contact step (iii). It is preferable that the dilution factor of the blood sample be not higher than the upper limit described above for avoiding spontaneous bilirubin consumption.

[2-3. Conditions in Contact Step (iii)]

In contact step (iii), both of non-reacted sample (a1) for route A and decomposed sample (b1) for route B receive addition of a buffer containing the fluorescent polypeptide UnaG. The buffer to which the fluorescent polypeptide UnaG is added may be selected, as appropriate, from the above examples of the buffer that may be used for first dilution. The fluorescent polypeptide UnaG and unconjugated bilirubin (iD-Bil) specifically bind to each other and form a complex. Thus, fluoresceinated non-reacted sample (a2) is obtained along route A and fluoresceinated decomposed sample (b2) is obtained along route B.

Contact step (iii) is carried out under conditions in which specific binding of the fluorescent polypeptide UnaG receives substantially no influence. Such conditions may include, for example, a temperature of not lower than 4° C. and not higher than 65° C., preferably not lower than 20° C. and not higher than 37° C., and an approximately neutral pH or a pH of, for example, not lower than 6.5 and not higher than 8.0, preferably not lower than 7.0 and not higher than 7.5, particularly preferably 7.4. In the case in which ascorbic acid is used as shown in the drawing, the pH tends to be low. The final concentration of ascorbic acid in contact step (iii) may be not lower than 0.01 wt % and not higher than 0.8 wt %, for example. It is preferable that the final concentration of ascorbic acid be not higher than 0.5 wt %, further preferably not higher than 0.25 wt %, even more preferably not higher than 0.2 wt %, further more preferably not higher than 0.05 wt %. It is preferable that the final concentration of ascorbic acid be not higher than the upper limit because when the final concentration of ascorbic acid is not higher than the upper limit, the specific binding of the fluorescent polypeptide UnaG receives substantially no influence. The reaction time may be not shorter than 20 seconds and not longer than 35 seconds, preferably not shorter than 25 seconds and not longer than 30 seconds.

In the reaction liquid in contact step (iii) after addition of the fluorescent polypeptide UnaG, it is greatly preferable that the blood sample be diluted to a degree where the inner-filter effect in fluorescence detection step (iv) is negligible. For example, the dilution factor of the blood sample in terms of serum may be not lower than 200 and not higher than 3200, preferably not lower than 400 and not higher than 1600, and may be, for example, 800.

The concentration of the buffer containing the fluorescent polypeptide UnaG and the amount of the buffer containing the fluorescent polypeptide UnaG to be added may be determined in consideration of the dilution factor and the pH of the blood sample described above. For example, the concentration of the buffer containing the fluorescent polypeptide UnaG may be determined so that the final concentration of UnaG after addition is not lower than 0.5 µM and not higher than 4 µM, preferably not lower than 1.0 µM and not higher than 3 µM, and is, for example, 2 µM from the viewpoints such as accurate measurement.

[2-4. Conditions in Detection Step (iv)]

In detection step (iv), each of fluoresceinated non-reacted sample (a2) for route A and fluoresceinated decomposed sample (b2) for route B is irradiated with an excitation light suitable for the fluorescence properties of the fluorescent polypeptide, followed by measurement of fluorescence intensity at a certain wavelength. The excitation wavelength may be not smaller than 480 nm and not greater than 520 nm, or not smaller than 490 nm and not greater than 510 nm, or not smaller than 494 nm and not greater than 504 nm. The detection wavelength of green fluorescence may be not smaller than 507 nm and not greater than 547 nm, or not smaller than 517 nm and not greater than 537 nm, or not smaller than 522 nm and not greater than 532 nm. In the case in which the fluorescent polypeptide UnaG is used, in particular, the excitation wavelength may be not smaller than 498 nm and not greater than 499 nm and the detection wavelength may be not smaller than 525 nm and not greater than 530 nm.

The means for fluorescence detection is not particularly limited. The fluorescence detection may be carried out with a UV transilluminator, an LED transilluminator, a fluorescence microscope, or a fluorescence detector, or by flow cytometry, for example.

In detection step (iv), the intensity of fluorescence emitted from fluoresceinated non-reacted sample (a2) along route A and the intensity of fluorescence emitted from fluoresceinated decomposed sample (b2) along route B are detected, and then the difference between the resulting values is calculated. The calculated value is regarded as the concentration of unbound bilirubin (UB). An absolute concentration of unbound bilirubin (UB) may be obtained by, for example, comparing the difference in fluorescence intensity with a calibration curve that has been generated in advance using a sample with a known concentration.

The difference in fluorescence intensity may be subjected to calibration, as appropriate. In the present invention, whole blood itself may be used as blood sample (a1) and subjected to measurement without treatment of the whole blood to obtain serum. So, in the case in which whole blood is used, the difference in fluorescence intensity may be subjected to hematocrit correction in this step so as to accurately determine the unbound bilirubin (UB) level.

[5. Unbound-Bilirubin Measurement Apparatus]

Figure 3:
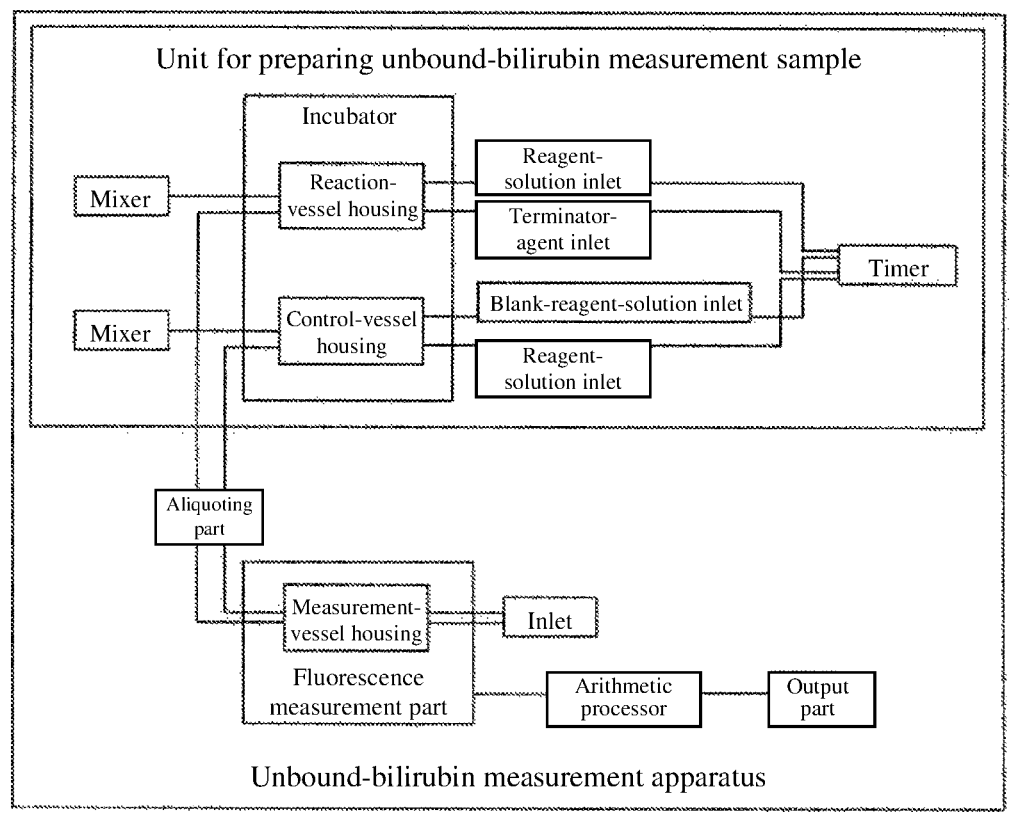
FIG. 3 shows a block diagram illustrating a unit for preparing an unbound-bilirubin measurement sample of the present invention and an unbound-bilirubin measurement apparatus of the present invention.

FIG. 3 shows a block diagram illustrating a unit for preparing an unbound-bilirubin measurement sample of the present invention and an unbound-bilirubin measurement apparatus of the present invention.

As shown in FIG. 3, the unit for preparing an unbound-bilirubin measurement sample has an incubator, a reagent-solution inlet, a blank-reagent-solution inlet, a timer, terminating-agent inlets, and mixers. This configuration enables automatic implementation of decomposition step (i) and decomposition termination step (ii) in the method of measuring unbound bilirubin.

The incubator has a reaction-vessel housing and a control-vessel housing. The reaction-vessel housing houses a reaction vessel, and the control-vessel housing houses a control vessel. The content of each vessel is maintained at a certain temperature with the use of the incubator.

The diluted blood sample added to the reaction vessel and the diluted blood sample added to the control vessel have the same composition. The diluted blood sample added to the reaction vessel takes route A shown in FIG. 2, and the diluted blood sample added to the control vessel takes route B shown in FIG. 2.

Each of the diluted blood sample added to the reaction vessel or the diluted blood sample added to the control vessel may have been, for example, mixed with a glucose-containing buffer. More specific procedure may be as follows: a blood sample and a glucose-containing buffer are mixed; and then the resulting mixture is divided, in other word, a portion of the mixture is put into the reaction vessel and another portion of the mixture is put into the control vessel. This procedure of mixing and dividing may be manually carried out, but the use of the unit for preparing an unbound-bilirubin measurement sample of the present invention does not intend to exclude automation of this procedure of mixing and dividing.

From the viewpoint of avoiding spontaneous bilirubin consumption in the reaction vessel and the control vessel, it is preferable that the incubator have a structure in which the reaction-vessel housing and the control-vessel housing are shielded from light.

The reagent-solution inlet is operative to add a certain amount of a reagent solution to the reaction vessel in the reaction-vessel housing, initiating decomposition step (i) that involves decomposition of unbound bilirubin in the reaction vessel. The reagent solution is a reagent solution for oxidative decomposition of unbound bilirubin. One of the mixers is operative to mix the content of the reaction vessel.

The reagent solution for oxidative decomposition of unbound bilirubin is, for example, a buffer containing GOD and POD. The reagent solution for oxidative decomposition of unbound bilirubin may be maintained at a certain temperature in the incubator.

The blank-reagent-solution inlet is operative to add a certain amount of a blank-reagent solution to the control vessel in the control-vessel housing. This means that decomposition step (i) involving decomposition of unbound bilirubin is not initiated in the control vessel. One of the mixers is operative to mix the content of the control vessel. The blank-reagent solution is, for example, a buffer that has a composition equivalent to that of the buffer containing GOD and POD from which both GOD and POD are removed. The blank-reagent solution may be maintained at a certain temperature in the incubator.

The timer is controlled so as to be actuated in response to the movement of the reagent-solution inlet or the blank-reagent-solution inlet. This control enables accurate measurement of the duration of decomposition step (i).

Each of the terminating-agent inlets is controlled to be actuated based on the time measured with the timer. More specifically, each of the terminating-agent inlets is controlled so as to add a certain amount of the oxidative-decomposition terminating agent to the reaction vessel or the control vessel when the timer counts a certain period of time. The certain period of time (preferably 30 seconds) refers to a time period considered to be required for completion of the decomposition of unbound bilirubin that has been free in the blood sample since the initiation of the reaction in decomposition step (i). Each mixer is operative to keep mixing the content of either the reaction vessel or the control vessel after the addition of the oxidative-decomposition terminating agent. In this way, the termination of the oxidative decomposition reaction of unbound bilirubin is carried out at the accurate timing. The oxidative-decomposition terminating agent, when used, may be in a state dissolved in the buffer, and the oxidative-decomposition terminating agent may be maintained at a certain temperature in the incubator.

As shown in FIG. 3, the unbound-bilirubin measurement apparatus of the present invention has the unit for preparing an unbound-bilirubin measurement sample, and further has a fluorescence measurement part, an arithmetic processor, and an output part. In this embodiment, the unbound-bilirubin measurement apparatus of the present invention further has an aliquoting part and an inlet.

The fluorescence measurement part has a measurement-vessel housing and has a known spectrophotometric system. It is preferable that a measurement vessel housed in the measurement-vessel housing have a structure that enables efficient observation of a plurality of samples for fluorescence detection, such as a multiple-well structure. The description of this embodiment adopts a multiple-well structure for the measurement vessel.

After the addition of the oxidative-decomposition terminating agent, a portion of the content of the reaction vessel (decomposed sample (b1), see FIGS. 1 and 2) is put into a well, and a portion of the content of the control vessel (non-reacted sample (a1), see FIGS. 1 and 2) is put into another well. This process may be manually carried out, or alternatively, may be carried out automatically with the action of the aliquoting part as in this embodiment. The aliquoting part may be controlled to be automatically actuated in response to the movement of the terminating-agent inlet or based on the time measured with the timer, or may be actuated based on manual command (for example, a command from a manual switch).

At the point of time at which the portion of the content of the reaction vessel and the portion of the content of the control vessel are put into each well (and before the addition of the polypeptide having fluorescence properties described below), the fluorescence measurement part may carry out blank measurement. This blank measurement may be carried out by manual command, or in this embodiment that involves use of the aliquoting part, may be carried out automatically in such a way that the fluorescence measurement part is controlled to be automatically actuated in response to the completion of the movement of the aliquoting part.

To the content of each well, the polypeptide having fluorescence properties is added. By this addition, contact step (iii) is initiated, in which fluorescence-measurement samples are obtained. The fluorescence-measurement samples refer to fluoresceinated non-reacted sample (a2) yielded in the well containing non-reacted sample (a1) and fluoresceinated decomposed sample (b2) yielded in the well containing decomposed sample (b1) (see FIGS. 1 and 2).

The addition of the polypeptide having fluorescence properties may be carried out manually, or may be carried out through an inlet as in this embodiment. This inlet may be controlled to be automatically actuated in response to, for example, the completion of the blank measurement described above, or may be actuated by manual command. An aspect of the polypeptide having fluorescence properties is, for example, a buffer containing a polypeptide that is essentially composed of UnaG. This buffer containing such a polypeptide may be maintained at a certain temperature in the incubator.

The fluorescence measurement part is operative to detect fluorescence that is emitted by the fluorescence-measurement samples, more specifically, emitted by fluoresceinated non-reacted sample (a2) and fluoresceinated decomposed sample (b2). This process is detection step (iv). This process may be carried out by manual command, or in this embodiment that involves use of the inlet, may be carried out in such a way that the fluorescence measurement part is controlled to be automatically actuated in response to the actuation of the inlet.

In the case in which detection step (iv) is carried out by the fluorescence measurement part that is automatically controlled, the timer may be controlled so as to be actuated in response to the addition of the polypeptide having fluorescence properties through the inlet, and the fluorescence measurement part may be controlled to be actuated based on the time measured with the timer. For example, the fluorescence measurement part may be controlled to be actuated to carry out fluorescence measurement when the time counted by the timer reaches a certain point of time (preferably not shorter than 10 minutes and not longer than 15 minutes) that is regarded as the point of time at which the polypeptide having fluorescence properties emits fluorescence at its maximum intensity. Alternatively, the fluorescence measurement part may be controlled to be continuously active to keep carrying out fluorescence measurement until the time counted with the timer reaches a certain period of time (preferably not shorter than 10 minutes and not longer than 15 minutes) that is regarded as the time period during which the polypeptide having fluorescence properties is emitting fluorescence at its maximum intensity.

The arithmetic processor is operative to determine the level of unbound bilirubin using at least the difference between the level of fluorescence attributable to the content of the reaction vessel and the level of fluorescence attributable to the content of the control vessel. In the case in which the fluorescence measurement part keep carrying out fluorescence measurement for a certain period of time (preferably not shorter than 10 minutes and not longer than 15 minutes) while the polypeptide having fluorescence properties is emitting fluorescence at its maximum intensity, the determination of the level of unbound bilirubin may be carried out after the arithmetic processor has identified the value of the maximum fluorescence intensity among all the measurement values of fluorescence intensity. In the case in which a plurality of identical samples are prepared as each of fluoresceinated non-reacted sample (a2) and fluoresceinated decomposed sample (b2) and thereby a plurality of values of fluorescence intensity are obtained for each type of the samples, the determination of the level of unbound bilirubin may be carried out after the arithmetic processor has determined a representative value (for example, the mean or the median) among all the measurement values of fluorescence intensity. If the blood sample is not serum but whole blood, the arithmetic processor may be operative to carry out hematocrit correction.

The output part is operative to display the resulting level of unbound bilirubin.

[6. Unbound-Bilirubin Measurement Kit]

An unbound-bilirubin measurement kit of the present invention is used for carrying out the method of measuring unbound bilirubin described above. The unbound-bilirubin measurement kit of the present invention contains at least the following items: oxidoreductase for oxidatively degrading unbound bilirubin; an oxidative-decomposition terminating agent for terminating the oxidative decomposition; and a polypeptide having an ability to specifically bind to unconjugated bilirubin and display fluorescence properties.

It is preferable that the oxidoreductase be peroxidase. From the viewpoints of storage stability and the like, it is preferable that the oxidoreductase be a form of lyophilizate. Alternatively, the oxidoreductase may be in a form of a liquid preparation that contains a buffer described below as solvent.

The oxidative-decomposition terminating agent may be selected, as appropriate, from the substances exemplified above for the unbound bilirubin measurement. The oxidative-decomposition terminating agent may be in a powder form or may be in a form of a liquid preparation that contains the buffer described above as solvent. It is preferable that the oxidative-decomposition terminating agent be an antioxidant, further preferably ascorbic acid. In the case in which the oxidative-decomposition terminating agent is ascorbic acid, in particular, a powder form is preferable from the viewpoints of storage stability and the like.

The polypeptide having fluorescence properties may be selected, as appropriate, from the substances exemplified above for the unbound bilirubin measurement. From the viewpoints of storage stability and the like, it is preferable that the polypeptide having fluorescence properties be a form of lyophilizate.

The unbound-bilirubin measurement kit may further contain glucose and glucose oxidase. The glucose may be in a powder form, or from the viewpoints of ease of use and/or accuracy in measurement, for example, the glucose may be in a form of a liquid preparation that contains the buffer described above as solvent. From the viewpoints of storage stability and the like, it is preferable that the glucose oxidase be a form of lyophilizate. Alternatively, the glucose oxidase may be in a form of a liquid preparation that contains the buffer described above as solvent.

The unbound-bilirubin measurement kit may further contain the following additional item: unbound bilirubin as a reference standard. The reference standard may be in a powder form, or may be in a form of a liquid preparation that contains the buffer described above as solvent.

Each of these items may be contained in a lightproof package, as appropriate. In addition, each of these items may be divided into a plurality of portions each in an amount suitable for a single batch, in other words, one kit may contain the plurality of portions.

The unbound-bilirubin measurement kit may further contain the following additional item: a buffer (such as PBS buffer (phosphate-buffered saline), acetate buffer, or Tris buffer) as a solvent or a diluent for at least one of the oxidoreductase, the oxidative-decomposition terminating agent, the polypeptide having fluorescence properties, the glucose, the glucose oxidase, and the reference standard.

The unbound-bilirubin measurement kit may further contain information regarding a protocol for the method of measuring unbound bilirubin described above. The information may be a printed material containing the protocol written on it, or may be a printed material containing information about the webpage where the protocol may be read on or obtained from the Internet or the like.

In the case in which the unbound-bilirubin measurement kit is specifically designed for the unbound-bilirubin measurement apparatus described above, for example, the unbound-bilirubin measurement kit may further contain the following additional item: a measurement vessel specifically designed for this purpose (a measurement vessel with a multiple-well structure, for example).

EXAMPLES

The present invention will be described below in a more specific way referring to examples. The scope of the present invention, however, is not limited to these examples.

An artificial bilirubin standard solution (sometimes simply called bilirubin standard solution) used in reference examples and examples below is a bilirubin standard solution manufactured by Arrows. As newborn serum, residual serum was used that was derived from a newborn admitted to the neonatal intensive care unit of Kobe University Hospital for use in a blood test for jaundice evaluation but left unused. Use of the residual serum was approved by the ethics committee of Kobe University Hospital. Use of the residual serum for basic research was approved by a legally authorized representative of the newborn.

Used as each of UnaG and UnaG-HisFLAG is a fluorescent polypeptide having an amino acid sequence represented by SEQ ID NO: 1 that was provided by the Institute of Physical and Chemical Research (RIKEN) Brain Science Institute.

As a GOD-POD enzyme solution, the following solution was used: 0.0068 mg of potassium dihydrogen phosphate and 0.720 mg of disodium hydrogen phosphate dodecahydrate were dissolved in purified water to obtain 25 µL of a liquid preparation; and in the resulting liquid preparation, 3.2 units of glucose oxidase lyophilizate and 3.2 units of peroxidase lyophilizate were dissolved. The buffer (Buffer) used as solvent and for dilution and enzyme dilution was a phosphate buffer (pH 7.4).

As a microplate reader, an SH-9000 manufactured by Corona Electric Co., Ltd. was used. Measurement of total bilirubin (TB) and unbound bilirubin (UB) was carried out with a UB analyzer (a specifically-designed measurement apparatus manufactured by Arrows). Measurement of total bilirubin (T-bil) and conjugated bilirubin (D-bil) was carried out with IatroQ T-BILII and IatroQ D-BBIL (A) (both manufactured by LSI Medience Corporation), respectively, that were based on the enzyme method. From the difference between the measurements of total bilirubin (TB) and unbound bilirubin (UB), the level of unconjugated bilirubin (iD-bil) was determined.

Figure 4:
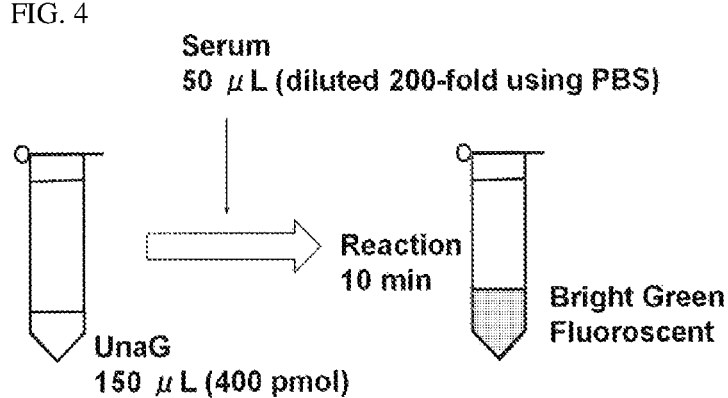
FIG. 4 schematically shows a protocol for the UnaG method carried out in Reference Example 1.

Reference Example 1: Comparison (1) Between UnaG Method Using UnaG and Enzyme Method in Term of Unconjugated Bilirubin Concentrations in Newborn Serum FIG. 4 schematically shows a protocol for the UnaG method carried out in Reference Example 1.
(Calibration Curve)
An artificial bilirubin standard solution was diluted serially so as to prepare a set of serially-diluted artificial bilirubin standard solutions that had bilirubin concentrations from 0.0 mg/dL to 33.6 mg/dL including a control.

A 50-μL portion of each of the serially-diluted artificial bilirubin standard solutions was mixed with 150 μL of an UnaG solution to prepare a total of 200 μL of a mixed solution. The final concentration of UnaG in the mixed solution was 2 μM.

Figure 5:
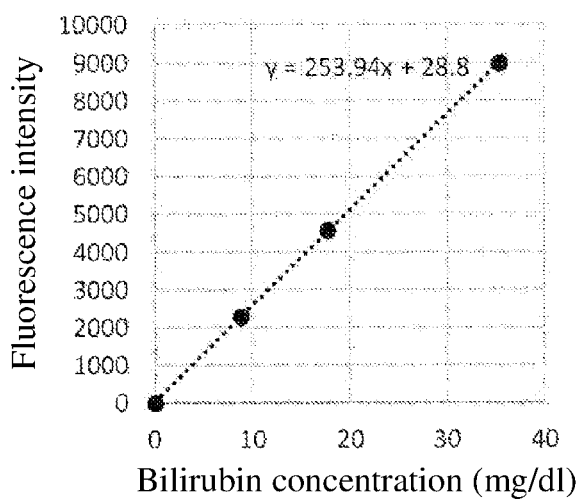
FIG. 5 shows a calibration curve obtained in Reference Example 1.

The fluorescence emitted from the mixed solution reached its maximum intensity 10 minutes after mixing. Therefore, 10 minutes after mixing, the intensity of the fluorescence was measured with a microplate reader. The excitation wavelength was 498 nm, and the fluorescence wavelength was 527 nm. The resulting measurements of fluorescence intensity were plotted as a function of the unconjugated bilirubin (iD-Bil) concentrations, and thus a calibration curve was generated. The resulting calibration curve is shown in FIG. 5.
(Specimen)
From 28 newborn cases, 48 specimens were obtained. Table 1 shows background information regarding the 28 newborn cases. Table 2 shows the number of days after birth at the time of serum collection and the levels of unconjugated bilirubin measured by the enzyme method, regarding the 48 specimens.

TABLE 1

|  | n = 28 |
| --- | --- |
| Number of weeks of gestation (weeks) | 37.5 (30.4-41.6) |
| Birth weight (g) | 2637 (1394-3838) | median (range)

TABLE 2

|  | n = 48 |
| --- | --- |
| Number of days after birth at serum collection | 5 (1-35) |
| iDB (mg/dL) | 11.8 (1.2-16.7) | median (range)

(Measurement of Unconjugated Bilirubin Concentrations)
Each of the newborn serum specimens described above was diluted 200-fold with PBS as shown in FIG. 4. A mixture of 50 μL of the resulting diluted newborn serum and 150 μL (400 mol) of an UnaG solution was subjected to reaction for 10 minutes, followed by measurement of fluorescence intensity in the same manner as above. From the resulting measurements, unconjugated bilirubin concentrations (unconjugated bilirubin concentrations measured by the UnaG method) were determined by using the calibration curve described above.

Correlation for the 48 specimens was evaluated, between the unconjugated bilirubin concentrations measured by the UnaG method and the unconjugated bilirubin concentrations measured by the enzyme method (obtained as the difference between the measurements of total bilirubin and the levels of conjugated bilirubin). A clear correlation was observed between these 2 methods in terms of the unconjugated bilirubin concentrations ($y=1.04x+0.18$, $R=0.954$, $P<0.001$).
(Influence of Phototherapy)
A similar correlation was found between a set of specimens (11 specimens) derived from newborns receiving phototherapy and a set of specimens (37 specimens) derived from newborns not receiving phototherapy. This result indicates that phototherapy did not affect the measurement system.

Reference Example 3 described below carried out the same comparison with an increased number of cases and an increased number of specimens.

Reference Example 2: Comparison (1) Between UnaG Method Using UnaG-HisFLAG and Enzyme Method in Terms of Unconjugated Bilirubin Concentrations in Newborn Serum (Specimen)
From 29 newborn cases, 53 specimens were obtained. Table 3 shows background information regarding the 29 newborn cases. Table 4 shows the number of days after birth at serum collection and the levels of unconjugated bilirubin measured by the enzyme method, regarding the 53 specimens.

TABLE 3

|  | n = 29 |
| --- | --- |
| Number of weeks of gestation (weeks) | 37.0 (27.7-40.0) |
| Birth weight (g) | 2508 (1014-3730) | median (range)

TABLE 4

|  | n = 53 |
| --- | --- |
| Number of days after birth at serum collection | 5 (2-27) |
| iDB (mg/dL) | 12.1 (1.3-20.2) | median (range)

(Measurement of Unconjugated Bilirubin)
A calibration curve was generated. Correlation between the UnaG method and the enzyme method in terms of the measurements of unconjugated bilirubin was evaluated in the same manner as in Reference Example 1 except that the specimens described above were used and the fluorescent protein used in the UnaG method was UnaG-HisFLAG. A clear correlation was observed between these 2 methods in terms of the unconjugated bilirubin concentrations ($y=1.02x-0.08$, $R=0.954$, $P<0.001$). UnaG-HisFLAG was a modified UnaG. More specifically, UnaG-HisFLAG was obtained by adding a FLAG tag to the UnaG used in Reference Example 1 via a histidine tag.
(Influence of Phototherapy)
A similar correlation was found between a set of specimens (19 specimens) derived from newborns receiving phototherapy and a set of specimens (34 specimens) derived from newborns not receiving phototherapy. This result indicates that phototherapy did not affect the measurement system.

Reference Example 3 described below carried out the same comparison with an increased number of cases and an increased number of specimens.

Reference Example 3: Comparison (2) Between UnaG Method Using UnaG and Enzyme Method in Terms of Unconjugated Bilirubin Concentrations in Newborn Serum, and Comparison (2) Between UnaG Method Using UnaG-HisFLAG and Enzyme Method in Terms of Unconjugated Bilirubin Concentrations in Newborn Serum (Specimen)

In this reference example, additional newborn cases and additional newborn serum specimens were used (in addition to the newborn cases and the serum specimens used in Reference Examples 1 and 2). In other words, this reference example used a total of 93 newborn cases including the newborn cases used in Reference Examples 1 and 2, and also used a total of 140 serum specimens (conjugated bilirubin<1.0 mg/dL) derived from the 93 newborn cases, including the serum specimens used in Reference Examples 1 and 2. Table 5 shows background information regarding the 93 newborn cases. Table 6 shows the number of days after birth at serum collection and the conjugated bilirubin levels measured by the enzyme method, regarding the 140 specimens.

TABLE 5

|  | n = 93 |
| --- | --- |
| Number of weeks of gestation (weeks) | 37 (27-41) |
| Birth weight (g) | 2760 (1014-3898) | median (range)

TABLE 6

|  | n = 140 |
| --- | --- |
| Number of days after birth at serum collection | 5 (1-35) |
| DB (mg/dL) | 0.2 (0.1-0.7) | median (range)

Figure 6:
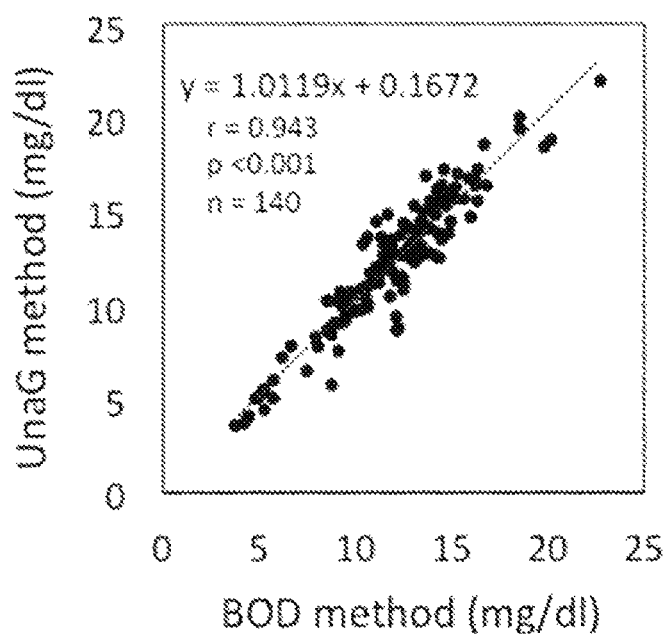
FIG. 6 shows the correlation observed in Reference Example 3, between the unconjugated bilirubin concentrations obtained by the UnaG method (using UnaG and using UnaG-HisFLAG) and the unconjugated bilirubin concentrations obtained by an enzyme method.

A calibration curve was generated. Correlation between the UnaG method and the enzyme method (BOD method) in terms of the measurements of unconjugated bilirubin was evaluated in the same manner as in Reference Example 2 except that the 140 specimens described above were used. The calibration curve was generated based on 72 specimens subjected to the UnaG method using UnaG and 68 specimens subjected to the UnaG method using UnaG-HisFLAG. FIG. 6 shows the result obtained from the 140 specimens. As shown in FIG. 6, a clear correlation was observed between these 2 methods in terms of the unconjugated bilirubin concentrations ($y=1.01x+0.17$, $r=0.943$, $P<0.001$).

(Measurement of Unconjugated Bilirubin, Comparison Between Use of UnaG and Use of UnaG-HisFLAG)

Figure 7:
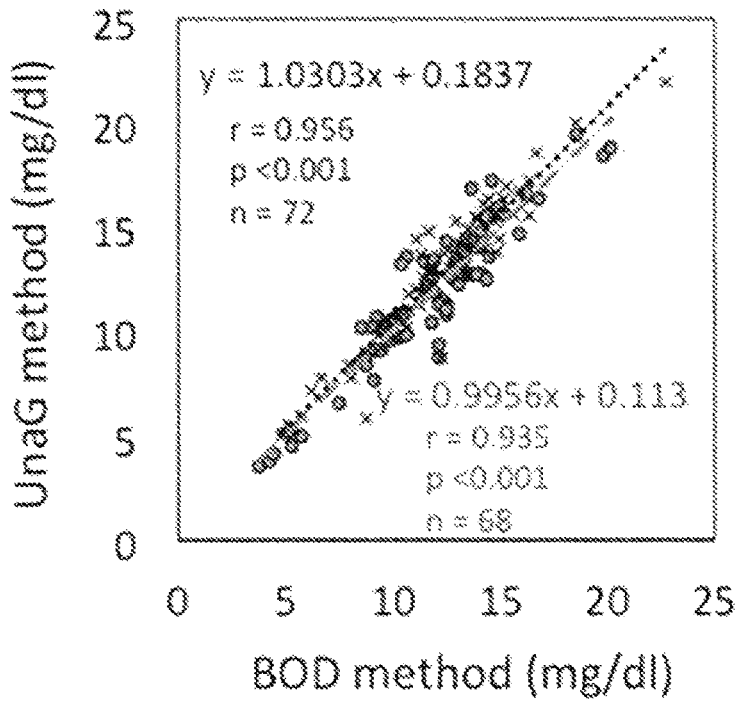
FIG. 7 shows the correlation observed in FIG. 6, in which the results from 72 specimens (plotted with x dots) to which the UnaG method using UnaG was employed are plotted distinguishably from the results from 68 specimens (plotted with ○ dots) to which the UnaG method using UnaG-HisFLAG was employed.

FIG. 7 shows the results from the 140 specimens shown in FIG. 6, in which the results from the 72 specimens to which UnaG was used are distinguishable the results from the 68 specimens to which UnaG-HisFLAG was used.

In FIG. 7, the results from the specimens (72 specimens) to which UnaG was used were plotted with x dots and the results from the specimens (68 specimens) to which UnaG-HisFLAG was used were plotted with ○ dots so that these 2 types were distinguishable from each other. As shown in FIG. 7, a clear correlation was observed between these 2 methods in terms of the unconjugated bilirubin concentrations in the specimen group (72 specimens, x dots) to which UnaG was used ($y=1.03x+0.18$, $r=0.956$, $p<0.001$); and, similarly, a clear correlation was observed between these 2 methods in terms of the unconjugated bilirubin concentrations in the specimen group (68 specimens, ○ dots) to which UnaG-HisFLAG was used ($y=0.996x+0.11$, $r=0.935$, $p<0.001$). There was no difference observed between the 2 correlations for the 2 specimen groups.

Besides, 5 types of serum specimens were collected at the same time of the same day, and these serum specimens were subjected to the UnaG method using UnaG or UnaG-HisFLAG. The results are shown in Table 7. As shown in Table 7, use of UnaG and use of UnaG-HisFLAG gave substantially the same unconjugated bilirubin concentrations.

TABLE 7

|  | Sample | | | | |
| --- | --- | --- | --- | --- | --- |
|  | #I | #II | #III | #IV | #V |
| UnaG | 3.4 | 6.6 | 8.5 | 12.2 | 13.8 |
| UnaG-His-FLAG | 3.3 | 6.4 | 8.5 | 12.3 | 13.7 |

(Influence of Phototherapy)

Figure 8:
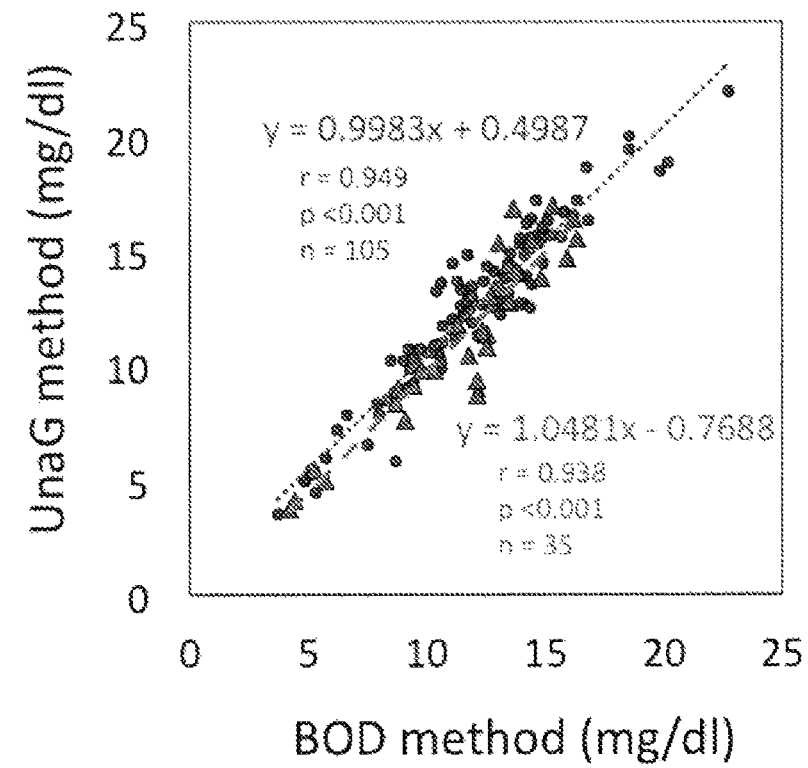
FIG. 8 shows the correlation observed in FIG. 6, in which the results from 35 specimens (plotted with triangular dots) derived from newborns receiving phototherapy are plotted distinguishably from the results from 105 specimens (plotted with circular dots) derived from newborns not receiving phototherapy.

The results from the 140 specimens described above were distinguishably plotted as follows: the results from a specimen group (105 specimens) collected while the donors were not receiving phototherapy were plotted with circular dots; and the results from a specimen group (35 specimens) collected while the donors were receiving phototherapy were plotted with triangular dots. The results are shown in FIG. 8. As shown in FIG. 8, no significant difference was observed between the 2 specimen groups. Thus, phototherapy did not affect the measurement system.

Reference Example 4: Comparison Between UnaG Method and Enzyme Method in Terms of Unconjugated Bilirubin Concentrations in Serum with High Conjugated Bilirubin Concentrations Table 8 shows the results of measurement of 14 specimens with high concentrations of conjugated bilirubin (conjugated bilirubin≥1.0 mg/dL). The table shows the following: comparison between the unconjugated bilirubin concentrations measured by the UnaG method and the concentrations measured by the enzyme method (BOD method), namely, the total bilirubin concentrations, the conjugated bilirubin concentrations, and the unconjugated bilirubin concentrations determined therefrom; and the difference between the unconjugated bilirubin concentrations measured by the UnaG method (using UnaG-HisFLAG) and the enzyme method. In Table 8, the total bilirubin concentrations, the conjugated bilirubin concentrations measured by the enzyme method (BOD (bilirubin oxidase) method), and the difference between these 2 sets of concentrations are shown along with the mean value and the standard deviation (SD). When the enzyme method was used, the unconjugated bilirubin concentrations were determined by the following expression.

[Unconjugated bilirubin]=[total bilirubin]−[conjugated bilirubin]

1 mg/dL=17.1 μM

Table 8 shows that the conjugated bilirubin concentrations measured by the enzyme method and the conjugated bilirubin concentrations measured by the UnaG method were similar to each other and no significant difference was observed therebetween (p=0.31). This result shows that the UnaG method enables direct measurement of unconjugated bilirubin regardless of the conjugated bilirubin concentrations.

TABLE 8

| Sample | BOD method (mg/dl) | | | UnaG method (mg/dl) | Difference (mg/dl) |
| --- | --- | --- | --- | --- | --- |
| | Total bilirubin | Conjugated bilirubin | Unconjugated bilirubin | | |
| #1 | 9.1 | 1.0 | 8.1 | 9.0 | −0.9 |
| #2 | 14.7 | 1.2 | 13.5 | 15.0 | −1.5 |
| #3 | 9.6 | 1.5 | 8.1 | 8.7 | −0.6 |
| #4 | 9.1 | 2.1 | 7.0 | 7.1 | −0.1 |
| #5 | 3.9 | 2.4 | 1.5 | 0.6 | 0.9 |
| #6 | 5.5 | 3.5 | 2.0 | 0.8 | 1.2 |
| #7 | 5.9 | 4.6 | 1.3 | 1.3 | 0.0 |
| #8 | 6.0 | 4.7 | 1.3 | 1.2 | 0.1 |
| #9 | 7.9 | 5.5 | 2.4 | 1.7 | 0.7 |
| #10 | 8.0 | 6.0 | 2.0 | 1.7 | 0.3 |
| #11 | 12.0 | 9.6 | 2.4 | 1.5 | 0.9 |
| #12 | 19.7 | 16.4 | 3.3 | 2.0 | 1.3 |
| #13 | 21.0 | 17.7 | 3.3 | 2.1 | 1.2 |
| #14 | 25.0 | 22.0 | 3.0 | 2.0 | 1.0 |
| Mean | | | 4.2 | 3.9 | 0.3 |
| SD | | | 3.6 | 4.3 | 0.9 |

Reference Example 5: Evaluation of Consistency of Bilirubin Measurement

Intra-day variation and inter-day variation in the measurement of unconjugated bilirubin by the UnaG method were checked using 5 newborn serum specimens. The results are shown in Table 9 as follows: A. Intra-day assay on intra-day variation; and B. Inter-day assay on inter-day variation. Table 9 shows the measurements of unconjugated bilirubin measured by the UnaG method (A: measured at different times, B: measured on different days), the median, the mean, the standard deviation (SD), and the coefficient of variation (CV), along with the measurements of unconjugated bilirubin measured by the enzyme method (BOD method).

The assay of intra-day variation was carried out to see if there was a difference in the iDB measurements of measurement samples that were prepared from the same serum preparation at different times. More specific procedure is as follows: serum was prepared; then a measurement sample was prepared from the serum every 20 minutes (approximately); and then measurement was carried out a total of 6 times.

The assay of inter-day variation was carried out to see if there was a difference in the iDB measurements of measurement samples that were prepared from the same serum preparation on different days. More specific procedure is as follows: serum was prepared; then a measurement sample was prepared from the serum every day; and then measurement was carried out for a total of 6 days.

Table 9 shows that the UnaG method yielded consistent measurements of unconjugated bilirubin in both of the intra-day assay and the inter-day assay.

TABLE 9

A. Intra-day assay

| Sample | BOD method (mg/dl) | UnaG method (mg/dl) | | | | | | Median | Mean | SD | CV |
| --- | --- | --- | --- | --- | --- | --- | --- | --- | --- | --- | --- |
| | | 1 | 2 | 3 | 4 | 5 | 6 | | | | |
| #A | 4.0 | 3.7 | 3.6 | 3.3 | 3.7 | 3.6 | 3.2 | 3.6 | 3.5 | 0.2 | 5.8 |
| #B | 11.5 | 11.1 | 10.7 | 10.7 | 10.6 | 10.7 | 10.7 | 10.7 | 10.7 | 0.2 | 1.5 |
| #C | 12.7 | 12.1 | 12.2 | 12.7 | 12.5 | 12.3 | 12.3 | 12.3 | 12.4 | 0.2 | 1.7 |
| #D | 15.0 | 15.2 | 14.8 | 15.1 | 14.8 | 14.3 | 14.1 | 14.8 | 14.7 | 0.4 | 3.0 |
| #E | 16.7 | 15.0 | 16.4 | 14.9 | 16.1 | 17.0 | 16.0 | 16.0 | 15.9 | 0.8 | 5.2 |

B. Intra-day assay

| Sample | BOD method (mg/dl) | UnaG method (mg/dl) | | | | | | Median | Mean | SD | CV |
| --- | --- | --- | --- | --- | --- | --- | --- | --- | --- | --- | --- |
| | | Day 1 | Day 2 | Day 3 | Day 4 | Day 5 | Day 6 | | | | |
| #A | 4.0 | 3.9 | 3.8 | 4.1 | 3.7 | 3.6 | 4.4 | 3.9 | 3.9 | 0.3 | 8.1 |
| #B | 11.5 | 13.5 | 10.8 | 12.4 | 11.1 | 11.7 | 11.8 | 11.7 | 11.9 | 1.0 | 8.3 |
| #C | 12.7 | 13.6 | 12.9 | 13.6 | 12.1 | 14.3 | 13.3 | 13.4 | 13.3 | 0.7 | 5.6 |
| #D | 15.0 | 14.7 | 15.2 | 14.1 | 15.3 | 15.1 | 14.5 | 14.9 | 14.8 | 0.5 | 3.2 |
| #E | 16.7 | 17.2 | 15.7 | 17.0 | 15.0 | 16.2 | 16.0 | 16.1 | 16.2 | 0.8 | 5.2 |

Summary of Reference Examples 1 to 5

Each of Reference Examples 1 to 3 above yielded a very clear correlation between the measurements of unconjugated bilirubin measured by the enzyme method and the measurements of unconjugated bilirubin measured by the UnaG method for a total of 140 serum specimens prepared from a total of 93 newborn cases.

Regarding the difference in the type of the fluorescent protein, Reference Examples 1 to 3 yielded substantially the same measurements of unconjugated bilirubin as for the UnaG method using the fluorescent protein UnaG and for the UnaG method using the fluorescent protein UnaG-HisFLAG.

Regarding the influence of phototherapy, Reference Examples 1 to 3 did not identify any obvious influence of phototherapy on either the UnaG method using the fluorescent protein UnaG or the UnaG method using the fluorescent protein UnaG-HisFLAG.

Regarding the influence of conjugated bilirubin concentrations, Reference Example 4 yielded substantially the same measurements for unconjugated bilirubin measured by the enzyme method and for unconjugated bilirubin measured by the UnaG method regarding 14 specimens with high concentrations of conjugated bilirubin.

In addition, Reference Example 5 yielded consistent measurements of unconjugated bilirubin at any point of time shorter than 24 hours from serum preparation and at any day after a lapse of 1 day or longer (not shorter than 1 day and not longer than 6 days).

These results readily suggest that the present invention is applicable to a specimen regardless of the level of conjugated bilirubin, the type of the fluorescent protein, the phototherapy history of the subject, and the time elapsed after serum preparation.

Reference Example 6: Measurement of Unconjugated Bilirubin Concentration in Hemolytic Specimen by UnaG Method This reference example assessed whether hemoglobin (hemolysis) in a specimen affects the measurement of unconjugated bilirubin (iDB) by the UnaG method.
(Preparation of Hemoglobin-Containing Solution)
1. From a healthy adult, 5 mL of whole blood was collected (blood gas analysis: Hb 16 g/dL).
2. Centrifugation was carried out, followed by sucking of the supernatant to leave red blood cells alone.
3. Addition of 2 mL of hemocytes and 3 mL of dH$_2$O was carried out to cause hemolysis. As a result, the total volume was 5 mL.
4. Thorough mixing was carried out, followed by centrifugation and transfer of the supernatant alone into a new tube.

By this procedure, cell membranes were removed from the red blood cells. As a result, the total volume became about 4 mL.
5. An XN-series 9000 analyzer (manufactured by Sysmex Corporation) based on the SLS-hemoglobin method was used to measure Hb concentrations (Hb 13.4).
6. The buffer (Buffer) was used to prepare serially-diluted Hb solutions with Hb 5 g/dL, Hb 2.5 g/dL, Hb 1 g/dL, and Hb 0.5 g/dL.
(Calibration Curve)
1. A bilirubin standard solution (unbound bilirubin reference standard, manufactured by Arrows) was prepared. The bilirubin standard solution contained 17.1 mg/dL of TB measured with a UB analyzer.
2. The bilirubin standard solution was serially diluted with the buffer (Buffer) so as to prepare a set of serially-diluted bilirubin standard solutions having bilirubin concentrations of 1.71 ng/μL, 0.855 ng/μL, and 0.4275 ng/μL. As a control, the buffer (Buffer) was used alone.
3. The buffer (Buffer) was used to prepare a 400 pmol/150 μL UnaG-His FLAG solution.
4. A mixture of 150 μL of the UnaG-His FLAG solution and 50 μL of one of the serially-diluted bilirubin standard solutions was subjected to measurement with a microplate reader. The measurement sensitivity was ×1. The fluorescence intensity (maximum fluorescence intensity) was measured 3 times for each serially-diluted bilirubin standard solution, 10 minutes after addition was started. Among the measurements, the median was used.
5. The bilirubin concentrations and the values of maximum fluorescence intensity were used to generate a calibration curve.
(Assay Using Standard Solution and Newborn Specimens)
1. Newborn serum specimens of 2 types (serum 225, serum 227) were prepared. As for each specimen, total bilirubin (T-bil) levels and conjugated bilirubin (D-bil) levels were measured by the enzyme method; unconjugated bilirubin (iD-bil) levels were determined from these levels; total bilirubin (TB) levels and unbound bilirubin levels (UB) were measured with a UB analyzer; and albumin (Alb) levels were obtained. These levels are shown in Table 10 along with TB and UB of the bilirubin standard solution.

TABLE 10

|  | T-bil mg/dL | D-bil mg/dL | iD-bil mg/dL | TB mg/dL | UB μg/dL | Alb mg/dL |
|---|---|---|---|---|---|---|
| Standard solution |  |  |  | 17.1 | 0.66 |  |
| Serum 225 | 13.4 | 0.3 | 13.1 | 12.6 | 0.57 | 3.7 |
| Serum 227 | 7.7 | 0.2 | 7.5 | 8.0 | 0.23 | 3.4 |

2. A 200-fold diluted newborn serum solution (containing hemoglobin) was prepared by mixing 10 μl of one of the newborn serum specimens, 10 μl of one of the hemoglobin-containing solutions prepared above by serial dilution, and 1980 μl of the buffer (Buffer). Each 200-fold diluted solution (containing hemoglobin) had a final hemoglobin concentration of 25 mg/dl, 12.5 mg/dl, 5 mg/dl, or 2.5 mg/dl.

A 200-fold diluted newborn serum solution (containing no hemoglobin) was prepared by mixing 10 μl of one of the newborn serum specimens and 1990 μl of the buffer (Buffer).

3. Similarly, 4 types of 200-fold diluted bilirubin standard solutions (containing hemoglobin) and 4 types of 200-fold diluted bilirubin standard solutions (containing no hemoglobin) were prepared.
4. A mixture of 150 μL of the UnaG-His FLAG solution used for generating a calibration curve and 50 μL of one of the 200-fold diluted newborn serum solutions or one of the 200-fold diluted bilirubin standard solutions was subjected to measurement of fluorescence intensity with a microplate reader. The measurement sensitivity was ×1. The fluorescence intensity (maximum fluorescence intensity) was measured 3 times for each serially-diluted solution, 10 minutes after addition was started. Among the measurements, the median was used.
5. The calibration curve described above was used to determine the iD-bil concentrations for the UnaG method.
(Results)

The diluted bilirubin standard solutions with different hemoglobin concentrations showed little differences in the iDB concentrations for the UnaG method.

Figure 9:
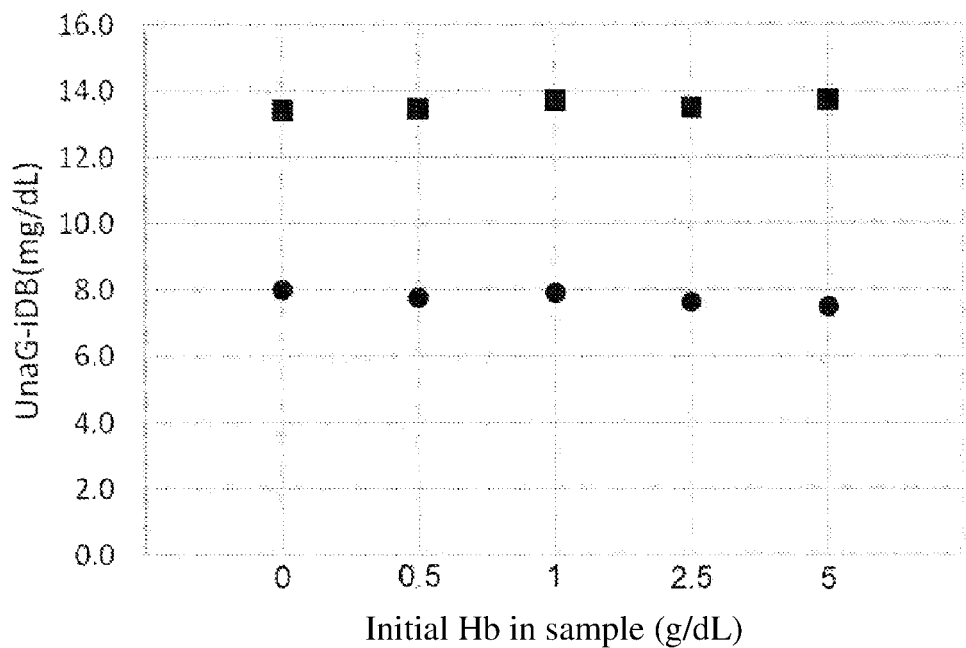
FIG. 9 is a graph obtained in Reference Example 6, which shows the unconjugated bilirubin concentrations determined by the UnaG method are not affected by hemoglobin concentrations in the newborn serum.

Similarly, the diluted newborn serum solutions with different hemoglobin concentrations showed little differences in the iDB concentrations for the UnaG method. The results are shown in Table 11 and FIG. 9 (square dots, serum 225; circular dots, serum 227).

TABLE 11

|  | Initial Hb concentration in sample (g/dL) | UnaG-iD-bil (mg/dL) | Enzyme method - iD-bil (mg/dL) |
|---|---|---|---|
| Serum 227 | 5 | 7.5 | 7.5 |
|  | 2.5 | 7.7 | 7.5 |
|  | 1 | 7.9 | 7.5 |
|  | 0.5 | 7.8 | 7.5 |
|  | 0 | 8.1 | 7.5 |
| Serum 225 | 5 | 13.8 | 13.1 |
|  | 2.5 | 13.5 | 13.1 |
|  | 1 | 13.8 | 13.1 |
|  | 0.5 | 13.5 | 13.1 |
|  | 0 | 13.5 | 13.1 |

Reference Example 7: Measurement of
Unconjugated Bilirubin Concentration in
Chyle-Containing Specimen by UnaG Method This reference example assessed whether chyle affects the measurement of unconjugated bilirubin (iDB) by the UnaG method.
(Preparation of Chyle Solution)
1. A 20% (20 g/100 mL, namely, 200 mg/mL) Intralipos injection was prepared.
2. The buffer (Buffer) was used to prepare Intralipos solutions with Intralipos concentrations of 20 mg/mL, 2 mg/mL, and 0.2 mg/mL. By this procedure, serially-diluted Intralipos solutions with Intralipos concentrations of 200 mg/mL (20%), 20 mg/mL (2%), 2 mg/mL (0.2%), and 0.2 mg/mL (0.02%) were prepared.
(Calibration Curve)
1. A bilirubin standard solution (unbound bilirubin reference standard, manufactured by Arrows) was prepared. The bilirubin standard solution contained 17.1 mg/dL of TB measured with a UB analyzer.
2. The bilirubin standard solution was serially diluted with the buffer (Buffer) so as to prepare a set of serially-diluted bilirubin standard solutions having bilirubin concentrations of 1.71 ng/μL, 0.855 ng/μL. and 0.4275 ng/μL. As a control, the buffer (Buffer) was used alone. 3. The buffer (Buffer) was used to prepare a 400 pmol/150 μL UnaG solution.
4. A mixture of 150 μL of UnaG and 50 μL of one of the serially-diluted bilirubin standard solutions was subjected to measurement with a microplate reader. The measurement sensitivity was ×1. The fluorescence intensity (maximum fluorescence intensity) was measured 3 times for each serially-diluted bilirubin standard solution, 10 minutes after addition was started. Among the measurements, the median was used.
5. The bilirubin concentrations and the values of maximum fluorescence intensity were used to generate a calibration curve.
(Assay Using Standard Solution and Newborn Specimens)
1. Newborn serum specimens of 2 types (serum 173, serum 200) were prepared. As for each specimen, total bilirubin (T-bil) levels and conjugated bilirubin (D-bil) levels were measured by the enzyme method; unconjugated bilirubin (iD-bil) levels were determined from these levels; total bilirubin (TB) levels and unbound bilirubin levels (UB) were measured with a UB analyzer; and albumin (Alb) levels were obtained. These levels are shown in Table 12 along with TB and UB of the bilirubin standard solution.

TABLE 12

|  | T-bil mg/dL | D-bil mg/dL | iD-bil mg/dL | TB mg/dL | UB μg/dL | Alb mg/dL |
|---|---|---|---|---|---|---|
| Standard solution |  |  |  | 17.1 | 0.66 |  |
| Serum 173 | 17 | 0.1 | 16.9 | 15.5 | 0.54 | 3.1 |
| Serum 200 | 8 | 0.2 | 7.8 | 8.1 | 0.33 | 3.6 |

2. A 200-fold diluted newborn serum solution (containing chyle) was prepared by mixing 10 μl of one of the newborn serum specimens, 10 μl of one of the chyle solutions prepared above, and 1980 μl of the buffer (Buffer). Each 200-fold diluted solution (containing chyle) had a final Intralipos concentration of 0.1%, 0.01%, 0.001%, or 0.0001%.

Figure 10:
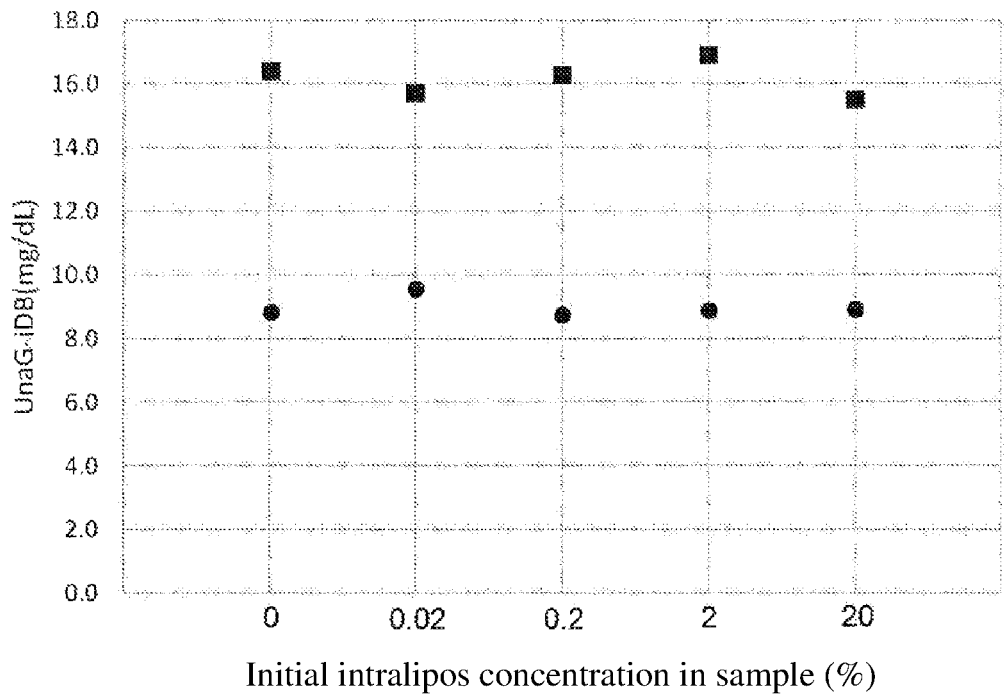
FIG. 10 is a graph obtained in Reference Example 7, which shows the unconjugated bilirubin concentrations determined by the UnaG method are not affected by chyle concentrations in the newborn serum.

A 200-fold diluted newborn serum solution (containing no chyle) was prepared by mixing 10 μl of one of the newborn serum specimens and 1990 μl of the buffer (Buffer).
3. Similarly, 4 types of 200-fold diluted bilirubin standard solutions (containing chyle) and 4 types of 200-fold diluted bilirubin standard solutions (containing no chyle) were prepared.
4. A mixture of 150 μL of the UnaG solution used for generating a calibration curve and 50 μL of one of the 200-fold diluted newborn serum solutions or one of the 200-fold diluted bilirubin standard solutions was subjected to measurement of fluorescence intensity with a microplate reader. The measurement sensitivity was ×1. The fluorescence intensity (maximum fluorescence intensity) was measured 3 times for each serially-diluted solution, 10 minutes after addition was started. Among the measurements, the median was used.
5. The calibration curve described above was used to determine the iD-bil concentrations for the UnaG method.
(Results)
The diluted bilirubin standard solutions with different Intralipos concentrations showed little differences in the iDB concentrations for the UnaG method.
Similarly, the diluted newborn serum solutions with different Intralipos concentrations showed little differences in the iDB concentrations for the UnaG method. The results are shown in Table 13 and FIG. 10 (square dots, serum 173; circular dots, serum 200).

TABLE 13

|  | Initial Intralipos concentration in sample (%) | UnaG-iD-bil (mg/dL) | Enzyme method - iD-bil (mg/dL) |
|---|---|---|---|
| Serum 173 | 20 | 15.5 | 16.9 |
|  | 2 | 17.0 | 16.9 |
|  | 0.2 | 16.3 | 16.9 |
|  | 0.02 | 15.8 | 16.9 |
|  | 0 | 16.5 | 16.9 |
| Serum 200 | 20 | 8.9 | 7.8 |
|  | 2 | 8.9 | 7.8 |
|  | 0.2 | 8.7 | 7.8 |
|  | 0.02 | 9.6 | 7.8 |
|  | 0 | 8.8 | 7.8 |

Reference Example 8: Measurement of
Unconjugated Bilirubin Concentration in
Ascorbic-Acid-Containing Specimen by UnaG
Method This reference example assessed whether ascorbic acid affects the measurement of unconjugated bilirubin (iDB) by the UnaG method.
(Preparation of Ascorbic Acid Solution)
1. In 10 mL of the buffer (Buffer), 1000 mg of ascorbic acid was dissolved. Thus, a 100 mg/mL ascorbic acid solution was prepared.
2. The buffer (Buffer) was used to prepare ascorbic acid solutions with ascorbic acid concentrations of 10 mg/mL, 1 mg/mL, and 0.1 mg/mL. By this procedure, serially-diluted ascorbic acid solutions with ascorbic acid concentrations of 100 mg/mL (10%), 10 mg/mL (1%), 1 mg/mL (0.1%), and 0.1 mg/mL (0.01%) were prepared.
(Assay Using Standard Solution and Newborn Specimens)
1. The same newborn serum specimens (serum 173, serum 200) as in Reference Example 7 were prepared.

2. A 200-fold diluted newborn serum solution (containing ascorbic acid) was prepared by mixing 10 µl of one of the newborn serum specimens, 200 µl of one of the ascorbic acid solutions prepared above, and 1790 µl of the buffer (Buffer). Each 200-fold diluted solution (containing ascorbic acid) had a final ascorbic acid concentration of 10 mg/mL, 1 mg/mL, 0.1 mg/mL, or 0.01 mg/mL.

A 200-fold diluted newborn serum solution (containing no ascorbic acid) was prepared by mixing 10 µl of one of the newborn serum specimens and 1990 µl of the buffer (Buffer).

3. Similarly, 4 types of 200-fold diluted bilirubin standard solutions (containing ascorbic acid) and 4 types of 200-fold diluted bilirubin standard solutions (containing no ascorbic acid) were prepared.

4. A mixture of 150 µL of the UnaG solution used for generating a calibration curve in Reference Example 7 and 50 µL of one of the 200-fold diluted newborn serum solutions or one of the 200-fold diluted bilirubin standard solutions was subjected to measurement of fluorescence intensity with a microplate reader. The measurement sensitivity was ×1. The fluorescence intensity (maximum fluorescence intensity) was measured 3 times for each serially-diluted solution, 10 minutes after addition was started. Among the measurements, the median was used.

5. The calibration curve in Reference Example 7 was used to determine the iD-bil concentrations for the UnaG method.

(Results)

The diluted bilirubin standard solutions with different ascorbic acid concentrations showed little differences in the iDB concentrations for the UnaG method.

Figure 11:
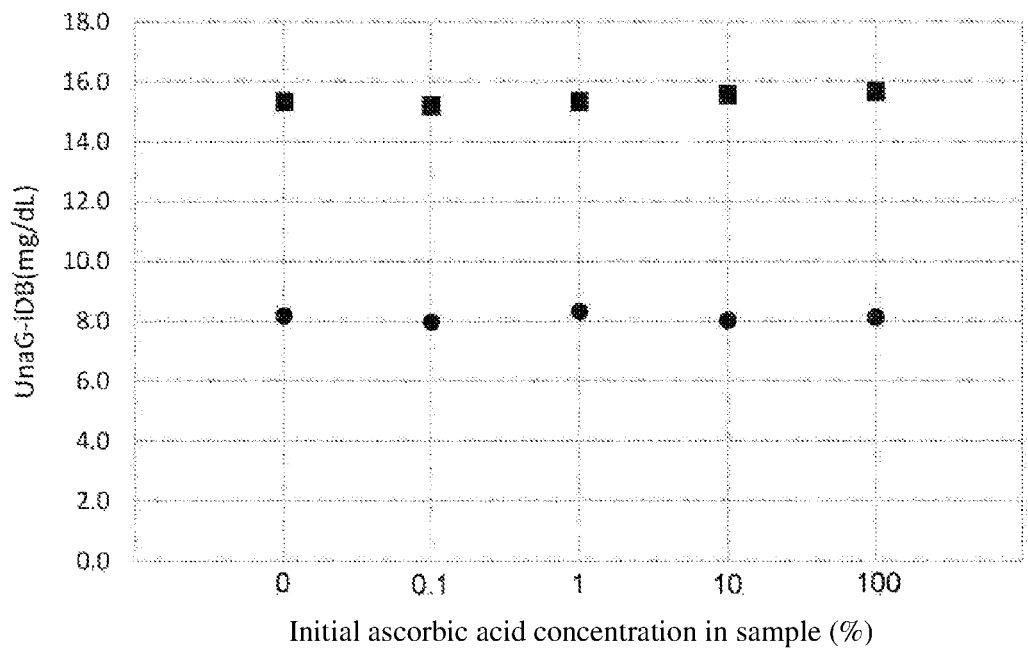
FIG. 11 is a graph obtained in Reference Example 8, which shows the unconjugated bilirubin concentrations determined by the UnaG method are not affected by ascorbic acid concentrations in the newborn serum.

Similarly, the diluted newborn serum solutions with different ascorbic acid concentrations showed little differences in the iDB concentrations for the UnaG method. The results are shown in Table 14 and FIG. 11 (square dots, serum 173; circular dots, serum 200).

TABLE 14

| | Initial ascorbic acid concentration in sample (mg/mL) | UnaG-iD-bil (mg/dL) | Enzyme method - iD-bil (mg/dL) |
|---|---|---|---|
| Serum 173 | 100 | 15.7 | 16.9 |
| | 10 | 15.6 | 16.9 |
| | 1 | 15.3 | 16.9 |
| | 0.1 | 15.3 | 16.9 |
| | 0 | 15.4 | 16.9 |
| Serum 200 | 100 | 8.2 | 7.8 |
| | 10 | 8.1 | 7.8 |
| | 1 | 8.3 | 7.8 |
| | 0.1 | 8.0 | 7.8 |
| | 0 | 8.2 | 7.8 |

Summary of Reference Examples 6 to 8

These reference examples identified no influence of hemoglobin, chyle, or ascorbic acid in the specimen on the measurement of unconjugated bilirubin by the UnaG method. These results readily suggest that the present invention is applicable to a specimen containing any of hemoglobin, chyle, and ascorbic acid.

Reference Example 9: UnaG Method Using Whole Blood (1)

From this reference example on, potential influence of hemocytes was checked using a serum sample prepared from a part of blood from a newborn and a whole blood sample that was another part of the blood.

In the same manner as in Reference Example 1, the serum sample and the whole blood sample were subjected to detection of fluorescence attributable to UnaG with a microplate reader and subjected to measurement of unconjugated bilirubin levels 3 times for each sample. As shown in Table 15, hematocrit (Ht) correction enabled measurement of unbound bilirubin levels in whole blood.

TABLE 15

| | Fluorescence intensity | | iD-bil concentration (mg/dL) | | |
|---|---|---|---|---|---|
| | Serum | Whole blood | Serum | Whole blood | After Ht correction* |
| 1st Measurement | 5759 | 3042 | 10.8 | 5.7 | 10.0 |
| 2nd Measurement | 6170 | 3098 | 11.6 | 5.8 | 10.2 |
| 3rd Measurement | 6270 | 2959 | 11.8 | 5.6 | 9.7 |

*(Levels after Ht correction) = (whole blood concentration)/(1 − Ht), Ht = 0.43

These results suggest that the present invention is applicable to a whole blood specimen.

Reference Example 10: UnaG Method Using Whole Blood (2)

From 18 newborn cases, 26 whole blood specimens were prepared. In the same manner as in Reference Example 1, a calibration curve was generated and the unconjugated bilirubin concentrations were obtained by the UnaG method. From each of the 26 whole blood specimens, a serum specimen was prepared. In the same manner as in Reference Example 1, the unconjugated bilirubin concentration in the serum specimen was obtained by the UnaG method and the enzyme method.

Figure 12:
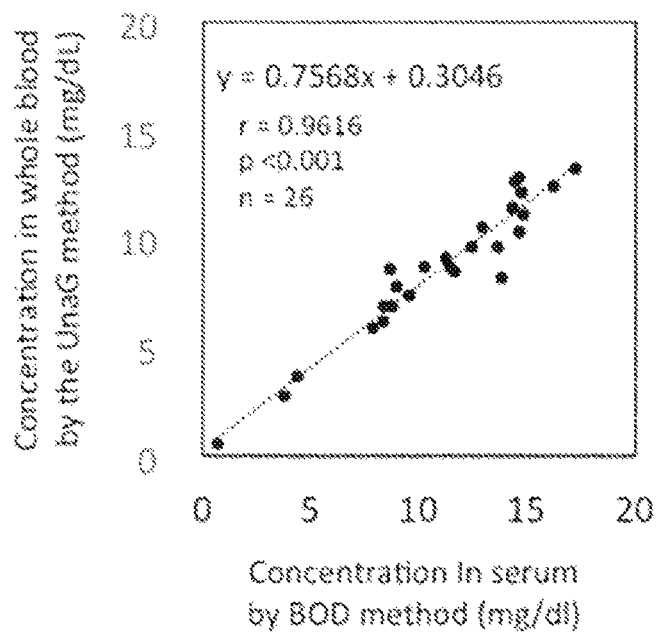
FIG. 12 shows the correlation observed in Reference Example 10, between the whole blood unconjugated bilirubin concentrations obtained by the UnaG method and the serum unconjugated bilirubin concentrations obtained by the enzyme method.

Correlation between the whole blood unconjugated bilirubin concentrations measured by the UnaG method (Concentration in whole blood by the UnaG method) and the serum unconjugated bilirubin concentrations measured by the enzyme method (Concentration in serum by BOD method) was evaluated. The results are shown in FIG. 12. FIG. 12 shows a clear correlation between these 2 methods in terms of the unconjugated bilirubin concentrations measured in these 2 specimens ($y=0.76x+0.30$, $r=0.962$, $p<0.001$).

Figure 13:
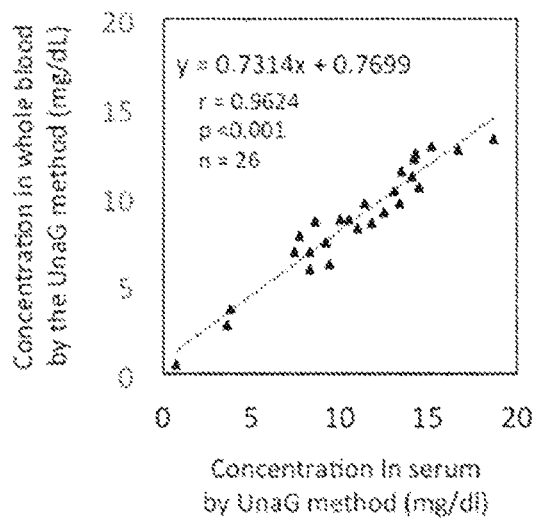
FIG. 13 shows the correlation observed in Reference Example 10, between the whole blood unconjugated bilirubin concentrations obtained by the UnaG method and the serum unconjugated bilirubin concentrations obtained by the UnaG method.

Correlation between the whole blood unconjugated bilirubin concentrations measured by the UnaG method (Concentration in whole blood by the UnaG method) and the serum unconjugated bilirubin concentrations measured by the UnaG method (Concentration in serum by UnaG method) was evaluated. The results are shown in FIG. 13. FIG. 13 shows a clear correlation between the unconjugated bilirubin concentrations measured in these 2 specimens ($y=0.73x+0.77$, $r=0.962$, $p<0.001$).

Reference Example 11: Statistical Analysis of UB/TB Ratio in Newborn Serum Measured with UB Analyzer In this reference example, 65 newborn serum specimens with high concentrations of conjugated bilirubin (high DB) and 245 newborn serum specimens with normal concentrations of conjugated bilirubin (normal DB) were used. The total bilirubin concentrations and the conjugated bilirubin concentrations in the specimens were measured by the enzyme method. The distribution of the ratio (conjugated bilirubin concentration)/(total bilirubin concentration) is shown in Table 16.

TABLE 16

| DB/TB | Lower than 5% | Not lower than 5% and lower than 10% | Not lower than 10% and lower than 20% | Not lower than 20% | Total |
|---|---|---|---|---|---|
| Normal DB | 245 | 0 | 0 | 0 | 245 |
| High DB | 16 | 34 | 8 | 7 | 65 |

Figure 14:
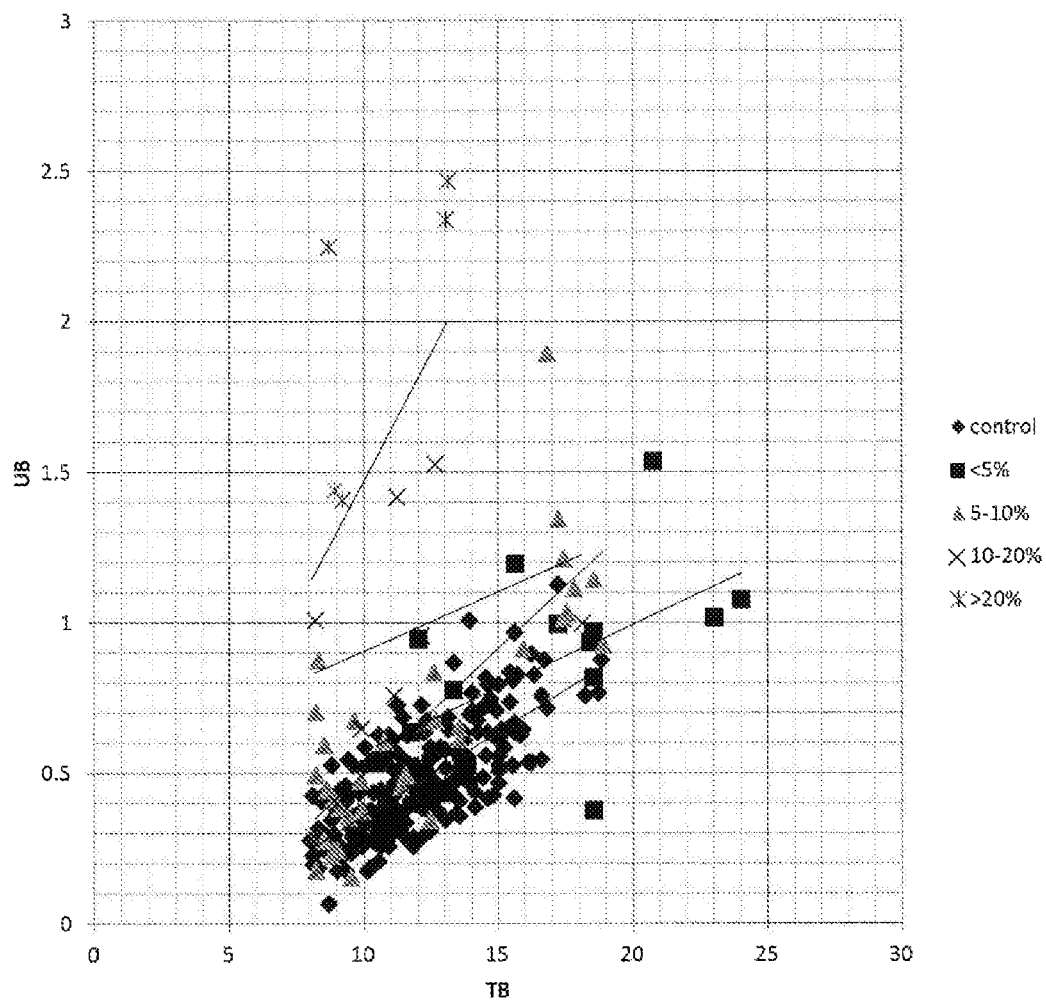
FIG. 14 shows the correlation observed in Reference Example 11, between the unbound bilirubin concentrations and the total bilirubin concentrations obtained with the use of a UB analyzer.

The specimens were subjected to measurement of unbound bilirubin concentrations with a UB analyzer so as to see if there was a correlation with the total bilirubin concentrations. The results are shown in FIG. 14. FIG. 14 shows a substantial correlation between TB and UB within the range of the ratio (conjugated bilirubin concentrations)/(total bilirubin concentrations) of lower than 5% and from not lower than 5% to lower than 10%. In the range of the ratio from not lower than 10% to lower than 20%, however, the correlation greatly lost its shape. The loss of correlation was more significant when the ratio was not lower than 20%.

Example 1: Measurement of Unbound Bilirubin by GOD-POD-UnaG Method

This example used newborn serum and measured unbound bilirubin by the method of the present invention.
(Calibration Curve for UnaG Method)
1. A bilirubin standard solution (unbound bilirubin reference standard, manufactured by Arrows) was prepared. The bilirubin standard solution contained 17.8 mg/dL of TB measured with a UB analyzer.
2. The bilirubin standard solution was serially diluted with the buffer (Buffer) so as to prepare a set of serially-diluted bilirubin standard solutions having bilirubin concentrations of 17.8 ng/μL, 8.9 ng/μL, and 4.45 ng/μL. As a control, the buffer (Buffer) was used alone.
3. The buffer (Buffer) was used to prepare a 400 μmol/195 μL UnaG-His FLAG solution. (His FLAG was an affinity purification tag added for large quantity production.)
4. A mixture of 195 μL of the UnaG-HisFLAG solution and 5 μL of one of the serially-diluted bilirubin standard solutions was subjected to measurement with a microplate reader. The measurement sensitivity was ×1. The fluorescence intensity was measured 3 times for each serially-diluted bilirubin standard solution, 15 minutes after addition was started. Among the measurements (of maximum fluorescence intensity), the median was used.
5. The bilirubin concentrations and the values of maximum fluorescence intensity were used to generate a calibration curve.
(Standard Solution and Newborn Specimens)
1. A bilirubin standard solution and 3 types of newborn serum specimens (serum 172, serum 211, serum 215) were prepared. As for each specimen, total bilirubin (T-bil) levels and conjugated bilirubin (D-bil) levels were measured by the enzyme method; unconjugated bilirubin (iD-bil) levels were determined from these levels; total bilirubin (TB) levels and unbound bilirubin (UB) levels were measured with a UB analyzer; and albumin (Alb) levels were obtained. These levels are shown in Table 17 along with TB and UB of the bilirubin standard solution.

TABLE 17

| | T-bil mg/dL | D-bil mg/dL | iD-bil mg/dL | TB mg/dL | UB μg/dL | Alb mg/dL |
|---|---|---|---|---|---|---|
| Standard solution | | | | 17.8 | 0.77 | |
| Serum 172 | 14.7 | 0.1 | 14.8 | 13.7 | 0.51 | 3.5 |
| Serum 211 | 15.9 | 0.1 | 15.8 | 15.3 | 0.75 | 3.6 |
| Serum 215 | 12.9 | 0.2 | 12.7 | 11.9 | 0.32 | 3.8 |

(Preparation of Reagents)
1. In 10 mL of the buffer (Buffer), 1600 mg of ascorbic acid was dissolved. Thus, a 16% (160 mg/mL) ascorbic-acid-containing buffer (Buffer) was prepared.
2. In 950 μL of an enzyme-solution diluent, 50 μL of the GOD-POD enzyme solution was dissolved. Thus, a 20-fold diluted GOD-POD solution was prepared.
3. To 10 mL of the buffer (Buffer), 500 mg of glucose was added. Thus, a 50 mg/ml glucose-containing buffer (Buffer) was prepared.
4. The 400 pmol/195 μL UnaG-HisFLAG solution (UnaG-HisFLAG solution) used above for generating a calibration curve for the UnaG method was prepared.
(Calibration Curve for GOD-POD-UnaG Method)
1. To 25 μL of the 50 mg/mL glucose-containing buffer (Buffer), 25 μL of the bilirubin standard solution (TB 17.8 mg/dL) was added. Thus, a (standard solution)-glucose mixed solution was prepared.
2. A 20 μL portion of the resulting (standard solution)-glucose mixed solution was transferred into a separate tube, to which 80 μL of the buffer (Buffer) was added. To the resulting mixture, 100 μL of the 16% ascorbic-acid-containing buffer (Buffer) was further added. Thus, a total of 200 μL of a 20-fold diluted 0-second-timepoint sample was obtained.
3. To another 20 JAL portion of the (standard solution)-glucose mixed solution, 80 μL of the 20-fold diluted GOD-POD solution was added. Then, 30 seconds later, 100 μL of the 16% ascorbic-acid-containing buffer (Buffer) was added. Thus, a total of 200 μL of a 20-fold diluted 30-second-timepoint sample was obtained.
4. A 5-μL portion was taken out of the 0-second-timepoint sample, and a 5-μL portion was taken out of the 30-second-timepoint sample. Each 5-μL portion was added in a well that contained 195 μL of the UnaG-HisFLAG solution, followed by measurement of fluorescence intensity. The fluorescence intensity was measured 3 times for each sample, 15 minutes after addition was started. Among the values of the maximum fluorescence intensity, the median was used (see Table 18).
5. The values of maximum fluorescence intensity for the 0-second-timepoint sample were used to generate a calibration curve.
6. The resulting calibration curve was used to determine the iD-bil concentrations in the 0-second-timepoint sample and the 30-second-timepoint sample (see Table 18).

TABLE 18

| Standard solution | | Fluorescence intensity (median) | iD-bil (mg/dl) | ∠iD-bil | ∠% |
|---|---|---|---|---|---|
| TB 17.7 UB 0.77 | 0 Second | 5185 | 17.7995194 | 3.669756 | 20.61716 |
| | 30 Seconds | 4116 | 14.12976313 | | |

The information described above was substituted into expression (I), and thus, the value K was obtained.

$$\Delta\text{iD-bil}/\Delta\text{Time} = K \times [\text{POD}] \times [\text{U-bil}] \quad (I)$$

The calculation gave a value K of 4.77.
(Measurement of Unbound Bilirubin in Serum by GOD-POD-UnaG Method)
1. To 25 μL of the 50 mg/mL glucose-containing buffer (Buffer), 25 μL of serum was added. Thus, a serum-glucose mixed solution was prepared. This means that the serum was diluted 2-fold.
2. To a 20-μL portion of the resulting serum-glucose mixed solution, 80 μL of the buffer (Buffer) was added (at this point, the serum was diluted 10-fold). To the resulting mixture, 100 μL of the 16% ascorbic-acid-containing buffer (Buffer) was further added (at this point, the serum was diluted 20-fold and 8% ascorbic acid was contained). Thus, a total of 200 μL of a 0-second-timepoint sample was obtained.
3. To another 20-μL portion of the serum-glucose mixed solution, 80 μL of the 20-fold diluted GOD-POD solution was added (at this point, the serum was diluted 10-fold). Then, 30 seconds later, 100 μL of the 16% ascorbic-acid-containing buffer (Buffer) was added (at this point, the serum was diluted 20-fold, and 8% ascorbic acid was contained). Thus, a total of 200 μL of a 30-second-timepoint sample was obtained. This means that at the time of decomposition reaction (more specifically, at the time of addition of 80 μL of the GOD-POD solution), the ratio of serum to undiluted (GOD-POD enzyme solution) GOD-POD was 10 μL to 4 μL. The amount of GOD-POD in 200 μL of the decomposition-reaction liquid product was 0.52 U.
4. A 5-μL portion was taken out of 200 μL of the 0-second-timepoint sample prepared in item 2 above, and a 5-μL portion was taken out of 200 μL of the 30-second-timepoint sample prepared in item 3 above. Each 5-μL portion was added in a well that contained 195 μL of the UnaG solution (at this point, the serum was diluted 800-fold, 0.2% ascorbic acid was contained, and pH was from 7.1 to 7.2), followed by measurement of fluorescence intensity with a microplate reader.
5. Each specimen was subjected to measurement of fluorescence intensity 3 times over the course of 15 minutes starting at the point of time of the addition. Among the values of maximum fluorescence intensity, the median was used (see Table 19).
6. The values of maximum fluorescence intensity and a calibration curve were used to determine the iD-bil concentrations in the 0-second-timepoint sample and the 30-second-timepoint sample (see Table 19).

TABLE 19

|  |  | Fluorescence intensity (median) | iD-bil (mg/dL) | ∠iD-bil | ∆% |
|---|---|---|---|---|---|
| Serum 172 TB 13.7 UB 0.51 | 0 Second 30 Seconds | 3954 3536 | 13.57363543 12.13868864 | 1.434947 | 10.57157 |
| Serum 211 TB 15.3 UB 0.75 | 0 Second 30 Seconds | 5023 4415 | 17.24339169 15.15619636 | 2.087195 | 12.10432 |
| Serum 215 TB 11.9 UB 0.32 | 0 Second 30 Seconds | 3977 3680 | 13.65259183 12.63302437 | 1.019567 | 7.467941 |

The value K (4.77) was calculated using the bilirubin standard solution and was used to determine the unbound bilirubin concentration ([U-bil]) for the GOD-POD-UnaG method by expression (I). The results show that the unbound bilirubin levels in each serum were as follows: 0.51 for serum 172; 0.75 for serum 211; and 0.32 for serum 215.

Example 2: Measurement of Unbound Bilirubin by GOD-POD-UnaG Method

This example used newborn serum and measured unbound bilirubin by the method of the present invention.
(Calibration Curve for UnaG Method)
1. A bilirubin standard solution (unbound bilirubin reference standard, manufactured by Arrows) was prepared. The bilirubin standard solution contained 17.7 mg/dL of TB measured with a UB analyzer.
2. The bilirubin standard solution was serially diluted with the buffer (Buffer) so as to prepare a set of serially-diluted bilirubin standard solutions having bilirubin concentrations of 4.435 ng/μL, 2.2175 ng/μL, and 1.10875 ng/μL. As a control, the buffer (Buffer) was used alone.
3. The buffer (Buffer) was used to prepare a 132.4 pmol/μL UnaG-His FLAG solution.
4. A mixture of 180 μL of the UnaG-HisFLAG solution and 20 μL of one of the serially-diluted bilirubin standard solutions was subjected to measurement with a microplate reader. The measurement sensitivity was ×1. The fluorescence intensity was measured 3 times for each serially-diluted bilirubin standard solution, 15 minutes after addition was started. Among the measurements (of maximum fluorescence intensity), the median was used.
5. The bilirubin concentrations and the values of maximum fluorescence intensity were used to generate a calibration curve.
(Standard Solution and Newborn Specimens)
1. A bilirubin standard solution and 4 types of newborn serum specimens (serum 179, serum 180, serum 181, serum 185) were prepared. As for each specimen, total bilirubin (T-bil) levels and conjugated bilirubin (D-bil) levels were measured by the enzyme method; unconjugated bilirubin (iD-bil) levels were determined from these levels; total bilirubin (TB) levels and unbound bilirubin levels (UB) were measured with a UB analyzer; and albumin (Alb) levels were obtained. These levels are shown in Table 20 along with TB and UB of the bilirubin standard solution.

TABLE 20

|  | T-bil mg/dL | D-bil mg/dL | iD-bil mg/dL | TB mg/dL | UB μg/dL | Alb mg/dL |
|---|---|---|---|---|---|---|
| Standard solution |  |  |  | 17.7 | 0.77 |  |
| Serum 179 | 16.3 | 0.2 | 16.1 | 14.9 | 0.74 | 3.5 |
| Serum 180 | 12.7 | 0.2 | 12.5 | 12.6 | 0.21 | 3.7 |
| Serum 181 | 12.3 | 0.1 | 12.2 | 12 | 0.33 | 3.4 |
| Serum 185 | 13.5 | 0.1 | 13.4 | 12.5 | 0.51 | 3.4 |

(Preparation of Reagents)
1. In 40 mL of the buffer (Buffer), 400 mg of ascorbic acid was dissolved. Thus, a 1% (10 mg/mL) ascorbic-acid-containing buffer (Buffer) was prepared.
2. A GOD-POD solution was prepared that was a UB analyzer reagent (Arrows) (see Table 21).
3. A 1 mg/ml glucose-containing buffer (Buffer) was prepared that was a UB analyzer reagent (Arrows) (see Table 21).
4. The 132.4 pmol/μL UnaG-HisFLAG solution (UnaG-HisFLAG solution) used above for generating a calibration curve for the UnaG method was prepared.

TABLE 21

| Reagent | Form | Component | Amount for single measurement |
|---|---|---|---|
| Buffer | Liquid preparation | Potassium dihydrogen phosphate | 2.72 mg |
| | | Disodium hydrogen phosphate dodecahydrate | 28.65 mg |
| | | Glucose | 1 mg |
| | | Purified water | Proper amount in 1 ml |
| Enzyme agent | Lyophilizate | Glucose oxidase | 3.2 International units |
| | | Peroxidase | 3.2 International units |
| Enzyme-agent solvent | Liquid preparation | Potassium dihydrogen phosphate | 0.068 mg |
| | | Disodium hydrogen phosphate dodecahydrate | 0.720 mg |
| | | Purified water | Proper amount in 25 μl |

(Calibration Curve for GOD-POD-UnaG Method)
1. To 100 μL of the 1 mg/mL glucose-containing buffer (Buffer), 20 μL of the bilirubin standard solution (iD-bil 17.7 mg/dL) was added. Thus, a (standard solution)-glucose mixed solution was prepared.
2. To the resulting (standard solution)-glucose mixed solution, 25 μL of the buffer (Buffer) was added. To the resulting mixture, 555 μL of the 1% ascorbic-acid-containing buffer (Buffer) was further added. Thus, a total of 1600 μL of a 80-fold diluted sample was obtained.
3. A 20-μL portion of the resulting 80-fold diluted sample was placed in a well in a UB analyzer, in which 180 μl of an UnaG solution had been loaded. Then, fluorescence intensity was measured.
4. The process described in item 3 above was repeated 3 times. In each session, fluorescence intensity was measured over the course of 10 minutes starting at the point of time of addition of the UnaG solution.
5. The values of maximum fluorescence intensity and the iD-bil concentrations were used to generate a calibration curve. The maximum fluorescence intensity here was the maximum value, which was also the median value, measured over the course of 10 minutes starting at the point of time of addition.

The results yielded the following relationship: (unconjugated bilirubin (iDB) concentration)=(maximum fluorescence intensity)/255.9. This agreed with the calibration curve shown in FIG. 5.

(Measurement of iD-Bil at 0 Second)
1. To 1000 μL of the 1 mg/mL glucose-containing buffer (Buffer), 20 μL of the bilirubin standard solution or serum (iD-bil 17.7 mg/dL) was added. Thus, a (standard solution)-glucose mixed solution was prepared.
2. To the resulting (standard solution)-glucose mixed solution, 25 μL of the buffer (Buffer) and 555 μL of the 1% ascorbic-acid-containing buffer (Buffer) were added simultaneously. Thus, a total of 1600 μL of a 80-fold diluted 0-second-timepoint sample was obtained.
3. Serum, the buffer (Buffer), the sample prior to ascorbic acid addition, and the sample after ascorbic acid addition were subjected to measurement of TB levels with a UB analyzer. A record of the results was kept.

(Measurement of iD-Bil at 20 Seconds)
1. To 1000 μL of the 1 mg/mL glucose-containing buffer (Buffer), 20 μL of the bilirubin standard solution or serum (iD-bil 17.7 mg/dL) was added. Thus, a (standard solution)-glucose mixed solution was prepared.
2. To the resulting (standard solution)-glucose mixed solution, 25 μL of the GOD-POD solution was added. After a lapse of 20 seconds, 555 μL of the 1% ascorbic-acid-containing buffer (Buffer) was added to the resulting mixture. Thus, a total of 1600 μL of a 80-fold diluted 20-second-timepoint sample was obtained.
3. Serum, the buffer (Buffer), the sample prior to ascorbic acid addition, and the sample after ascorbic acid addition were subjected to measurement of TB levels with a UB analyzer. A record of the results was kept.

At this point, 12.5 μl of undiluted GOD-POD was contained per 10 μl of serum; 3.2 U of GOD-POD was contained in 1600 μL of the 20-second-timepoint sample; and the final concentration of ascorbic acid after the addition of the ascorbic-acid-containing buffer (Buffer) was 0.35%.

(Method of Analysis)
1. A 20-μl portion was taken out of 1600 μL of the 0-second-timepoint sample (hereinafter, simply called 0-second sample), and a 20-μl portion was taken out of 1600 μl of the 20-second-timepoint sample (hereinafter, simply called 20-second sample). Each 20-μl portion was placed in a well that contained 180 μl of an UnaG solution, followed by measurement of fluorescence intensity. The 20-μl portion thus added was 80-fold diluted serum, the final concentration of ascorbic acid was 0.035 wt %, and the pH was not lower than 7.30 and not higher than 7.35.
2. Each sample was subjected to measurement of fluorescence intensity 3 times over the course of 10 minutes starting at the time point of the addition.
3. From the resulting values of maximum fluorescence intensity, the iD-bil concentrations at 0 second (0-second concentrations) and the iD-bil concentrations at 20 seconds (20-second concentrations) were determined.
4. The 0-second concentrations and the 20-second concentrations in the standard solution and expression (I) were used to determine the value K.

$$\Delta \text{iD-bil}/\Delta \text{Time} = K \times [\text{POD}] \times [\text{U-bil}] \quad (I)$$

5. The 0-second concentrations and the 20-second concentrations in the newborn serum, the value K determined in item 4 above, and expression (I) were used to determine the U-bil concentrations.
6. The U-bil concentrations determined in item 5 above and the U-bil concentrations determined with the use of a UB analyzer were compared so as to see if there was a correlation therebetween.

(Additional Assay)
In the same manner as above, a 30-second-timepoint sample (more specifically, a sample obtained by addition of the 1% ascorbic-acid-containing buffer (Buffer) after a lapse of 20 seconds) was prepared. Then, the cases in which the decomposition reaction time was 20 seconds (see Table 22) and the cases in which the decomposition reaction time was 30 seconds (see Table 23) were compared to see which of these cases had more consistent ΔTB % values.

TABLE 22

| Glucose buffer (Buffer) | GOD-POD | TB - 0 second | TB - 20 second | ∠TB | ∠TB % |
|---|---|---|---|---|---|
| Undiluted 25 μl | 995 μL | 25 μL | 22.5 | 18.2 | 4.3 | 19.1% |
| Undiluted 20 μl | 1000 μL | 25 μL | 16.8 | 12.8 | 4.0 | 23.8% |
| Undiluted 15 μl | 1005 μL | 25 μL | 13.0 | 9.8 | 3.2 | 24.6% |

TABLE 23

| Glucose buffer (Buffer) | GOD-POD | TB - 0 second | TB - 30 second | ⌃TB | ⌃TB % |
|---|---|---|---|---|---|
| Undiluted 25 μl | 995 μL | 25 μL | 21.7 | 15.7 | 6.0 | 27.6% |
| Undiluted 20 μl | 1000 μL | 25 μL | 16.6 | 11.3 | 5.3 | 32.0% |
| Undiluted 15 μl | 1005 μL | 25 μL | 13.2 | 8.6 | 4.6 | 35.0% |

The results in Tables 22 and 23 were considered, and the decision was made to use the 20-second sample (obtained after a decomposition reaction time of 20 seconds).
(Results)
1. Standard Solution
Table 24 shows the TB concentrations and the UB concentrations in the standard solution.

TABLE 24

| Standard solution | TB | UB |
|---|---|---|
| 1st Measurement | 17.0 | 0.74 |
| 2nd Measurement | 16.5 | 0.71 |
| 3rd Measurement | 16.1 | 0.69 |
| Median | 16.5 | 0.71 |

Table 25 shows the measurements thus recorded. In Table 25, "Value after conversion" refers to the value obtained by multiplying the volume difference by 1600/1045 (the same applies to all applicable tables).

TABLE 25

| | TB Concentration on display | 0-Second sample | 20-Second sample | ∠TB | ∠TB % |
|---|---|---|---|---|---|
| 1st Measurement | Upon addition of 20 μL of serum | 16.8 | 16.6 | | |
| | At 20 seconds | 16.8 | 12.9 | 3.3 | 19.6 |
| | After ascorbic acid addition | 10.6 | 8.5 | 2.1 | 19.8 |
| | Value after conversion | 16.2 | 13.0 | 3.2 | 19.8 |
| 2nd Measurement | Upon addition of 20 μL of serum | 16.7 | 16.7 | | |
| | At 20 seconds | 16.3 | 13.0 | 3.3 | 19.8 |
| | After ascorbic acid addition | 10.6 | 8.5 | 2.1 | 19.7 |
| | Value after conversion | 16.2 | 13.0 | 3.2 | 22.4 |
| 3rd Measurement | Upon addition of 20 μL of serum | 17.1 | 16.8 | | |
| | At 20 seconds | 16.7 | 13.2 | 3.5 | 21.0 |
| | After ascorbic acid addition | 10.8 | 8.8 | 2.0 | 18.5 |
| | Value after conversion | 16.5 | 13.5 | 3.0 | 18.4 |

Table 26 shows the measurements obtained after addition of the UnaG solution. From Table 26, it has been confirmed that either of the TB concentrations measured with a UB analyzer and the iDB concentrations obtained by using UnaG had consistent values of A %, which were near 20%.

TABLE 26

| | 0-Second sample | iDB - 0 second | 20-Second sample | iDB - 20 second | ⌃DB | ⌃DB % |
|---|---|---|---|---|---|---|
| UnaG - 1st measurement | | | | | | |
| #1 | 4628 | 18.1 | 3584 | 14.0 | | |
| #2 | 4551 | 17.8 | 3526 | 13.8 | | |
| #3 | 4475 | 17.5 | 3527 | 13.8 | | |
| Median | 4551 | 17.8 | 3527 | 13.8 | 4.0 | 22.5 |
| UnaG - 2nd measurement | | | | | | |
| #1 | 4749 | 18.6 | 3487 | 13.6 | | |
| #2 | 4494 | 17.6 | 3504 | 13.7 | | |
| #3 | 4483 | 17.5 | 3471 | 13.6 | | |
| Median | 4494 | 17.6 | 3487 | 13.6 | 3.9 | 22.4 |

TABLE 26-continued

| | 0-Second sample | iDB - 0 second | 20-Second sample | iDB - 20 second | ∠DB | ∠DB % |
|---|---|---|---|---|---|---|
| UnaG - 3rd measurement | | | | | | |
| #1 | 4462 | 17.4 | 3511 | 13.7 | | |
| #2 | 4530 | 17.7 | 3549 | 13.9 | | |
| #3 | 4671 | 18.3 | 3576 | 14.0 | | |
| Median | 4530 | 17.7 | 3549 | 13.9 | 3.8 | 21.7 |

The value K was calculated as follows.

$$\Delta TB/\Delta t = K \times [POD] \times [UB]$$

$$K = \Delta TB/\Delta t[POD]/[UB]$$

Both of Δt and [POD] were constant in this experiment system and therefore defined as 1.

As a result, the following expression was obtained: $K = \Delta TB/0.71$.

The resulting value K was used as the iDB concentrations and the TB concentrations for the GOD-POD-UnaG method.

TABLE 27

| ∠TB as base for calculation | K |
|---|---|
| 20-Second-timepoint TB concentrations | 4.65 |
| Value after conversion after ascorbic acid addition | 4.51 |
| UnaG method - iDB concentrations | 5.49 |

2. Serum 179

Table 28 shows the TB concentrations and the UB concentrations of serum 179.

TABLE 28

| Serum 179 | TB | UB |
|---|---|---|
| 1st Measurement | 16.8 | 0.93 |
| 2nd Measurement | 15.5 | 0.89 |

TABLE 28-continued

| Serum 179 | TB | UB |
|---|---|---|
| 3rd Measurement | 15.9 | 0.84 |
| Median | 15.9 | 0.89 |

Table 29 shows the measurements thus recorded.

TABLE 29

| | TB Concentration on display | 0-Second sample | 20-Second sample | ⊿TB | ⊿TB % |
|---|---|---|---|---|---|
| 1st Measurement | Upon addition of 20 μL of serum | 15.8 | 15.8 | | |
| | At 20 seconds | 15.2 | 11.4 | 3.8 | 25.0 |
| | After ascorbic acid addition | 9.8 | 7.7 | 2.1 | 21.4 |
| | Value after conversion | 15.0 | 11.8 | 3.2 | 21.3 |
| 2nd Measurement | Upon addition of 20 μL of serum | 16.1 | 15.9 | | |
| | At 20 seconds | 15.4 | 11.2 | 4.2 | 19.8 |
| | After ascorbic acid addition | 9.9 | 7.4 | 2.5 | 25.3 |
| | Value after conversion | 15.2 | 11.3 | 3.9 | 25.7 |

Table 30 shows measurements after the addition of the UnaG solution.

TABLE 30

| | 0-Second sample | iDB - 0 second | 20-Second sample | IDB - 20 second | ⊿DB | ⊿DB % |
|---|---|---|---|---|---|---|
| UnaG - 1st measurement | | | | | | |
| #1 | 3808 | 14.9 | 2486 | 9.7 | | |
| #2 | 3383 | 13.2 | 2290 | 8.9 | | |
| #3 | 3766 | 14.7 | 2509 | 9.8 | | |
| Median | 3766 | 14.7 | 2486 | 9.7 | 5.0 | 31.0 |
| UnaG - 2nd measurement | | | | | | |
| #1 | 4058 | 15.9 | 2507 | 9.8 | | |
| #2 | 3897 | 15.2 | 2450 | 9.6 | | |
| #3 | 3816 | 14.9 | 2449 | 9.6 | | |
| Median | 3897 | 15.2 | 2450 | 9.6 | 5.7 | 37.1 |

3. Serum 181

Table 31 shows the TB concentrations and the UB concentrations of serum 181.

TABLE 31

| Serum 181 | TB | UB |
|---|---|---|
| 1st Measurement | 12.9 | 0.52 |
| 2nd Measurement | 13.0 | 0.53 |
| 3rd Measurement | — | — |
| Median | 13.0 | 0.53 |

Table 32 shows the measurements thus recorded.

TABLE 32

| | TB Concentration on display | 0-Second sample | 20-Second sample | ∠TB | ∠TB % |
|---|---|---|---|---|---|
| 1st Measurement | Upon addition of 20 µL of serum | 13.0 | 13.2 | | |
| | At 20 seconds | 12.6 | 10.3 | 2.3 | 18.2 |
| | After ascorbic acid addition | 8.2 | 6.7 | 1.5 | 18.3 |
| | Value after conversion | 12.6 | 10.3 | 2.3 | 18.3 |
| 2nd Measurement | Upon addition of 20 µL of serum | 13.1 | 13.0 | | |
| | At 20 seconds | 12.7 | 10.2 | 2.5 | 19.7 |
| | After ascorbic acid addition | 8.1 | 6.6 | 1.5 | 18.5 |
| | Value after conversion | 12.4 | 10.1 | 2.3 | 18.5 |

Table 33 shows measurements after the addition of the UnaG solution.

TABLE 33

| | 0-Second sample | iDB - 0 second | 20-Second sample | iDB - 20 second | ∠iDB | ∠iDB % |
|---|---|---|---|---|---|---|
| UnaG - 1st measurement | | | | | | |
| #1 | 2916 | 11.4 | 2233 | 8.7 | | |
| #2 | 2909 | 11.4 | 1764 | 6.9 | | |
| #3 | 2947 | 11.5 | 2271 | 8.9 | | |
| Median | 2916 | 11.4 | 2233 | 8.7 | 2.7 | 23.4 |
| UnaG - 2nd measurement | | | | | | |
| #1 | 3039 | 11.9 | 2074 | 8.1 | | |
| #2 | 3012 | 11.8 | 1656 | 6.5 | | |
| #3 | 2994 | 11.7 | 2022 | 7.9 | | |
| Median | 3012 | 11.8 | 2022 | 7.9 | 3.9 | 32.9 |

4. Serum 185

Table 34 shows the TB concentrations and the UB concentrations of serum 185.

TABLE 34

| Serum 185 | TB | UB |
|---|---|---|
| 1st Measurement | 14.2 | 0.6 |
| 2nd Measurement | — | — |
| 3rd Measurement | — | — |
| Median | 14.2 | 0.60 |

Table 35 shows the measurements thus recorded.

TABLE 35

| | TB Concentration on display | 0-Second sample | 20-Second sample | ∠TB | ∠TB % |
|---|---|---|---|---|---|
| 1st Measurement | Upon addition of 20 µL of serum | 14.8 | 14.2 | | |
| | At 20 seconds | 14.3 | 10.9 | 3.4 | 23.8 |
| | After ascorbic acid addition | 9.3 | 7.0 | 2.3 | 24.7 |
| | Value after conversion | 14.2 | 10.7 | 3.5 | 24.6 |
| 2nd Measurement | Upon addition of 20 µL of serum | 14.2 | 14.0 | | |
| | At 20 seconds | 13.8 | 10.7 | 2.5 | 22.5 |
| | After ascorbic acid addition | 9.0 | 7.1 | 1.9 | 21.1 |
| | Value after conversion | 13.8 | 10.9 | 2.9 | 21.0 |

Table 36 shows measurements after the addition of the UnaG solution.

TABLE 36

| | 0-Second sample | iDB - 0 second | 20-Second sample | iDB - 20 second | ∠DB | ∠DB % |
|---|---|---|---|---|---|---|
| UnaG - 1st measurement | | | | | | |
| #1 | 3455 | 13.5 | 2384 | 9.3 | | |
| #2 | 3238 | 12.7 | 2285 | 8.9 | | |
| #3 | 3167 | 12.4 | 2313 | 9.0 | | |
| Median | 3238 | 12.7 | 2313 | 9.0 | 3.6 | 28.6 |

TABLE 36-continued

|  | 0-Second sample | iDB - 0 second | 20-Second sample | iDB - 20 second | ∠DB | ∠DB % |
|---|---|---|---|---|---|---|
| UnaG - 2nd measurement | | | | | | |
| #1 | 3175 | 12.4 | 2235 | 8.7 | | |
| #2 | 2705 | 10.6 | 2393 | 9.4 | | |
| #3 | 3128 | 12.2 | 2185 | 8.5 | | |
| Median | 3128 | 12.2 | 2235 | 8.7 | 3.5 | 28.5 |

5. Serum 180

Table 37 shows the TB concentrations and the UB concentrations of serum 180.

TABLE 37

| Serum 180 | TB | UB |
|---|---|---|
| 1st Measurement | 14.2 | 0.33 |
| 2nd Measurement | 14.2 | 0.33 |
| 3rd Measurement | — | — |
| Median | 14.2 | 0.33 |

Table 38 shows the measurements thus recorded.

TABLE 38

| | TB Concentration on display | 0-Second sample | 20-Second sample | ∠TB | ∠TB % |
|---|---|---|---|---|---|
| 1st Measurement | Upon addition of 20 μL of serum | 14.5 | 14.2 | | |
| | At 20 seconds | 14.0 | 12.0 | 2.0 | 14.3 |
| | After ascorbic acid addition | 9.1 | 7.9 | 1.2 | 13.2 |
| | Value after conversion | 13.9 | 12.1 | 1.8 | 12.9 |
| 2nd Measurement | Upon addition of 20 μL of serum | 14.7 | 14.7 | | |
| | At 20 seconds | 14.3 | 12.8 | 1.5 | 10.5 |
| | After ascorbic acid addition | 9.1 | 8.3 | 0.8 | 9.6 |
| | Value after conversion | 13.9 | 12.7 | 1.2 | 8.6 |

Table 39 shows measurements after the addition of the UnaG solution.

TABLE 39

|  | 0-Second sample | iDB - 0 seconds | 20-Second sample | iDB - 20 seconds | ∠DB | ∠DB % |
|---|---|---|---|---|---|---|
| UnaG - 1st measurement | | | | | | |
| #1 | 3018 | 11.8 | 2587 | 10.1 | | |
| #2 | 2980 | 11.6 | 2469 | 9.6 | | |
| #3 | 3001 | 11.7 | 2121 | 8.3 | | |
| Median | 3001 | 11.7 | 2469 | 9.6 | 2.1 | 17.7 |
| UnaG - 2nd measurement | | | | | | |
| #1 | 3126 | 12.2 | 2589 | 10.1 | | |
| #2 | 3160 | 12.3 | 2560 | 10.0 | | |
| #3 | 3107 | 12.1 | 2536 | 9.9 | | |
| Median | 3126 | 12.2 | 2560 | 10.0 | 2.2 | 18.1 |

(Calculation of UB Concentrations)

1. Table 40 shows the UB concentrations measured with a UB analyzer by the conventional measurement method (the GOD-POD method) and the UB concentrations (ΔTB/4.65) calculated from the TB concentrations at 20 seconds.

TABLE 40

| Serum | UB Concentrations | ∠TB | ∠TB % | UB = ∠TB/ 4.65 |
|---|---|---|---|---|
| 179-1st Measurement | 0.89 | 3.8 | 25.0 | 0.82 |
| 179-2nd Measurement | 0.89 | 4.2 | 19.8 | 0.90 |
| 181-1st Measurement | 0.53 | 2.3 | 18.2 | 0.49 |
| 181-2nd Measurement | 0.53 | 2.5 | 19.7 | 0.54 |
| 185-1st Measurement | 0.60 | 3.4 | 23.8 | 0.73 |
| 185-2nd Meausrement | 0.60 | 2.5 | 22.5 | 0.54 |
| 180-1st Measurement | 0.33 | 2.0 | 14.3 | 0.43 |
| 180-2nd Measurement | 0.33 | 1.5 | 10.5 | 0.32 |

Figure 15:
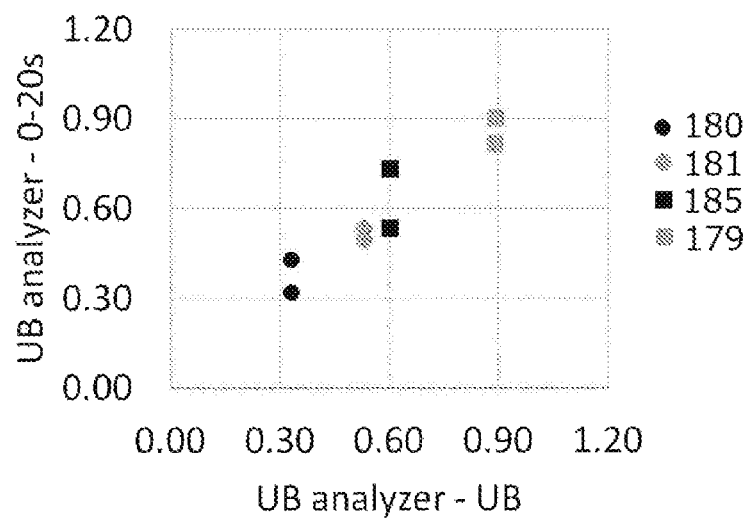
FIG. 15 shows the correlation observed between the UB concentrations (UB analyzer UB) measured with a UB analyzer by the conventional measurement method and the UB concentrations (UB analyzer—0-20 s) calculated from TB concentrations.

FIG. 15 shows a correlation between the UB concentrations (UB analyzer UB) measured with a UB analyzer by the conventional measurement method and the UB concentrations (UB analyzer—0-20 s) calculated from the TB concentrations. As shown in FIG. 15, these 2 sets of concentrations showed a clear correlation. This result has proven that the UB concentrations can be calculated from the change (ΔTB, the difference between the 0-second concentrations and the 20-second concentrations) in the TB concentrations measured with a UB analyzer after addition of the GOD-POD solution.

2. Table 41 shows the UB concentrations measured with a UB analyzer by the conventional measurement method (the GOD-POD method) and the UB concentrations (ΔTB/4.51) calculated from the values after conversion after ascorbic acid addition.

TABLE 41

| Serum | UB Concentrations | ∠TB | ∠TB % | UB = ∠TB/ 4.51 |
|---|---|---|---|---|
| 179-1st Measurement | 0.89 | 3.2 | 21.3 | 0.71 |
| 179-2nd Measurement | 0.89 | 3.9 | 25.7 | 0.86 |
| 181-1st Measurement | 0.53 | 2.3 | 18.3 | 0.51 |
| 181-2nd Measurement | 0.53 | 2.3 | 18.5 | 0.51 |
| 185-1st Measurement | 0.60 | 3.5 | 24.6 | 0.78 |
| 185-2nd Measurement | 0.60 | 2.9 | 21.0 | 0.64 |
| 180-1st Measurement | 0.33 | 1.8 | 12.9 | 0.40 |
| 180-2nd Measurement | 0.33 | 1.2 | 8.6 | 0.27 |

Figure 16:
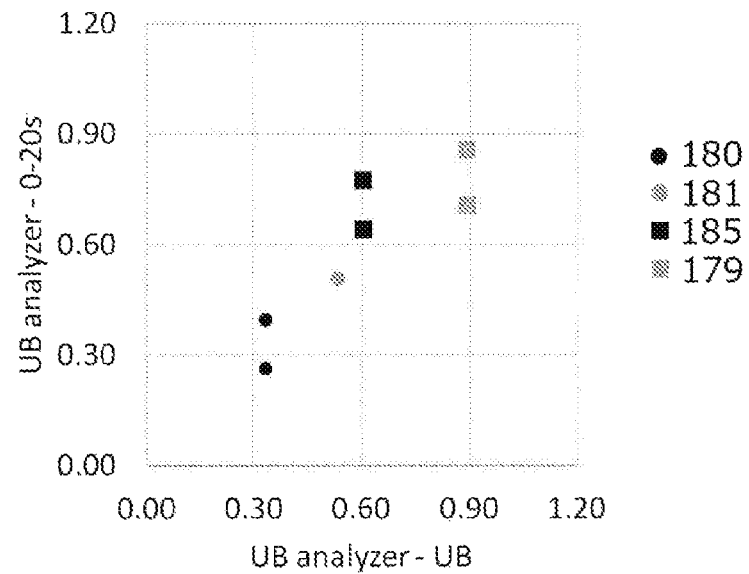
FIG. 16 shows the correlation observed between the UB concentrations (UB analyzer UB) measured with a UB analyzer by the conventional measurement method and the UB concentrations (UB analyzer—0-20 s) calculated from the values (after conversion) obtained after ascorbic acid addition.

FIG. 16 shows a correlation between the UB concentrations (UB analyzer UB) measured with a UB analyzer by the conventional measurement method and the UB concentrations (UB analyzer—0-20 s) calculated from the values after conversion after ascorbic acid addition. As shown in FIG. 16, these 2 sets of concentrations showed a clear correlation. This result has proven that the UB concentrations can be calculated from the ΔTB values, which is the difference between the 0-second concentrations and the 20-second concentrations measured with a UB analyzer after termination of the reaction caused by ascorbic acid addition.

Figure 17:
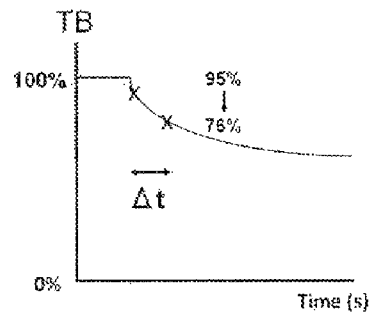
FIG. 17 describes method (a) of calculating UB concentrations by the conventional measurement method and method (b) of calculating UB concentrations in the present invention.
Figure 17:
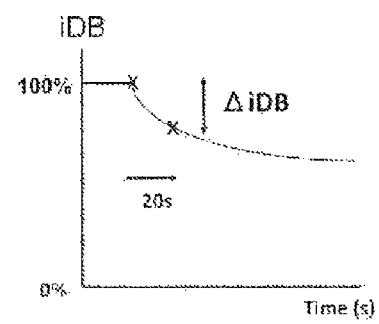

In the conventional measurement method (the GOD-POD method) with the use of a UB analyzer, the UB concentrations are calculated from the time required for the TB concentrations to decrease from 95% to 76% after addition of the GOD-POD solution (see FIG. 17(a)). The present invention, as proven by items 1 and 2 above, enables calculation of the UB concentrations either from the ΔTB values (measured by a colorimetric method) at 20 seconds starting from the addition of the GOD-POD solution, or from the ΔiDB values (measured by the UnaG method) at 20 seconds starting from the addition of the GOD-POD solution (see FIG. 17(b)).

3. Table 42 shows the UB concentrations measured with a UB analyzer by the conventional measurement method (the GOD-POD method) and the UB concentrations (ΔTB/5.49) calculated from the iDB concentrations measured by the GOD-POD-UnaG method.

TABLE 42

| Serum | UB Concentrations | ∠TB | ∠TB % | UB = ∠TB/ 5.49 |
|---|---|---|---|---|
| 179-1st Measurement | 0.89 | 5.0 | 34.0 | 0.91 |
| 179-2nd Measurement | 0.89 | 5.7 | 37.1 | 1.04 |
| 181-1st Measurement | 0.53 | 2.7 | 23.4 | 0.49 |
| 181-2nd Measurement | 0.53 | 3.9 | 32.9 | 0.71 |
| 185-1st Measurement | 0.60 | 3.6 | 28.6 | 0.66 |
| 185-2nd Measurement | 0.60 | 3.5 | 28.5 | 0.64 |
| 180-1st Measurement | 0.33 | 2.1 | 17.7 | 0.38 |
| 180-2nd Measurement | 0.33 | 2.2 | 18.1 | 0.40 |

Figure 18:
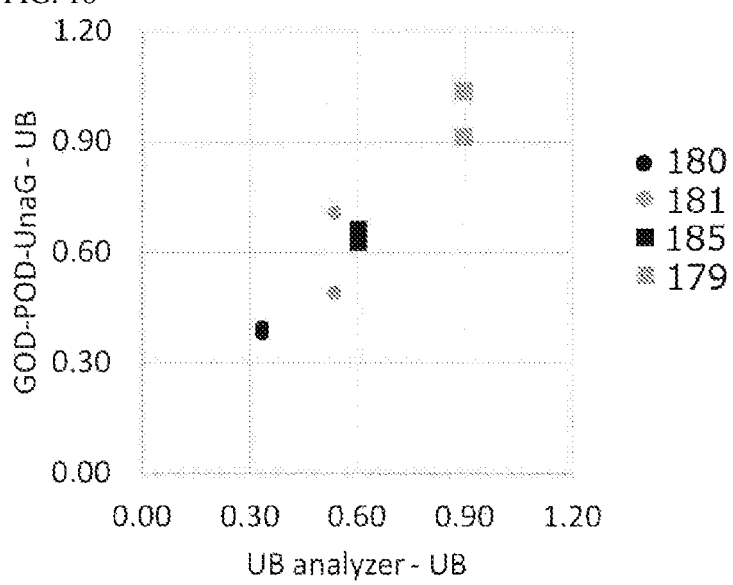
FIG. 18 shows the correlation observed between the UB concentrations (UB analyzer UB) measured with a UB analyzer by the conventional measurement method and the UB concentrations (GOD-POD-UnaG-UB) calculated from the iDB concentrations attributable to the GOD-POD-UnaG method.

FIG. 18 shows a correlation between the UB concentrations (UB analyzer UB) measured with a UB analyzer by the conventional measurement method and the UB concentrations (GOD-POD-UnaG-UB) calculated from the iDB concentrations measured by the GOD-POD-UnaG method. As shown in FIG. 18, these 2 sets of concentrations showed a clear correlation. This result has proven that the UB concentrations can be calculated from the iDB concentrations measured with a UB analyzer by the UnaG method after termination of the reaction caused by ascorbic acid addition.

Example 3: Measurement of Unbound Bilirubin by GOD-POD-UnaG Method (Case of Low DB Concentrations)

(Specimen)

Assay was carried out on 45 serum specimens with low DB concentrations (DB<1.0 mg/dL) derived from 33 newborn cases. Table 43 shows background information regarding the 33 cases. Table 44 shows the number of days after birth at serum collection and the unconjugated bilirubin levels measured by the enzyme method, regarding the 45 specimens.

TABLE 43

| | n = 33 |
|---|---|
| Number of weeks of gestation (weeks) | 38 (35-41) |
| Birth weight (g) | 2844 (2054-3474) | median (range)

TABLE 44

| | n = 45 |
|---|---|
| Number of days after birth at serum collection | 5 (1-19) |
| iDB (mg/dL) | 13.5 (3.1-23.1) |
| DB (mg/dL) | 0.2 (0.1-0.4) | median (range)

(Measurement of Unconjugated Bilirubin, Comparison to GOD-POD Method)

Figure 19:
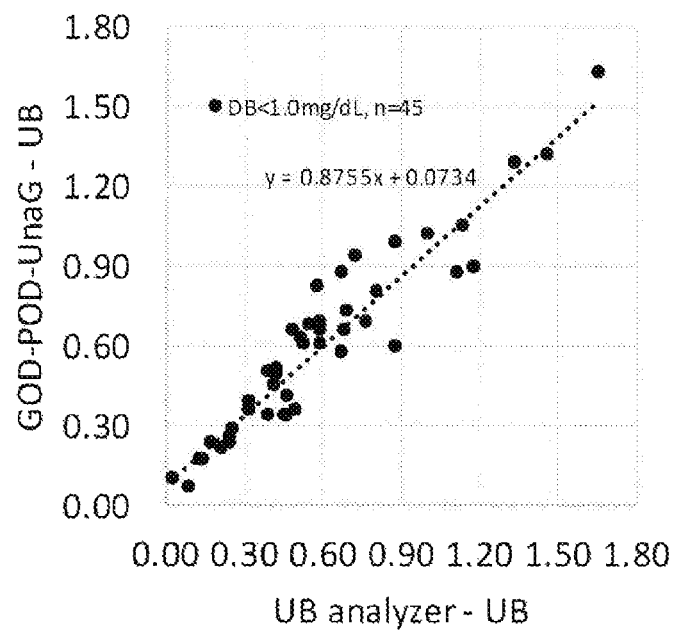
FIG. 19 shows the correlation observed in serum specimens with low DB concentrations in Example 3, between the UB concentrations (UB analyzer UB) measured with a UB analyzer by the conventional measurement method and the UB concentrations (GOD-POD-UnaG-UB) calculated from the iDB concentrations attributable to the GOD-POD-UnaG method.

In the same manner as in Example 2, the 45 specimens were subjected to measurement of unbound bilirubin (UB) by the GOD-POD-UnaG method of the present invention. For reference purposes, the 45 specimens were also subjected to measurement of UB with a UB analyzer (by the GOD-POD method). The UB concentrations measured by the GOD-POD-UnaG method and the UB concentrations measured by the GOD-POD method were compared to see if there was a correlation therebetween. As shown in FIG. 19, a clear correlation was observed between these 2 methods in terms of the UB concentrations (y=0.876x+0.07, r=0.947, P<0.001).

Example 4: Measurement of Unbound Bilirubin by GOD-POD-UnaG Method (Case of High DB Concentrations)

(Specimen)

Assay was carried out on 11 serum specimens with high DB concentrations (DB≥1.0 mg/dL) derived from 4 newborn cases. Table 45 shows specimen numbers of the 11 specimens; case numbers (case No. 1 regarding trisomy 18, case Nos. 2 and 3 regarding congenital cytomegalovirus infection, case No. 3 regarding methylmalonic acidemia); the number of weeks of gestation; birth weight (BW); the number of days after birth at serum collection; total bilirubin levels (T-bil (mg/dL)) and conjugated bilirubin levels (D-bil (mg/dL)) measured by the enzyme method, unconjugated bilirubin levels (iD-bil (mg/dL)) determined from these levels, and the ratio (DB/TB (%)) of conjugated bilirubin levels to total bilirubin levels; total bilirubin levels (TB (mg/dL)) and unbound bilirubin (unconjugated bilirubin) levels (UB (μg/dL)) measured with a UB analyzer; and albumin levels (Alb (g/dL)).

TABLE 45

| Specimen No. | Case No. | Number of weeks | BW | Number of days | T-bil | D-bil | iD-bil | DB/TB | TB | UB | Alb |
|---|---|---|---|---|---|---|---|---|---|---|---|
| 308 | 1 | 30 w 5 d | 744 | 3 | 9.1 | 1 | 8.1 | 11.0 | 9.6 | 0.7 | 2.6 |
| 309 | 2 | 39 w 2 d | 2054 | 4 | 7.9 | 5.5 | 2.4 | 69.6 | 9.1 | 0.73 | 3.1 |
| 310 | 1 | 30 w 5 d | 744 | 4 | 14.7 | 1.2 | 13.5 | 8.2 | 15.1 | 1.9 | 4.1 |
| 314 | 1 | 30 w 5 d | 744 | 5 | 9.1 | 2.1 | 7 | 23.1 | 10.4 | 0.99 | 2.7 |
| 315 | 1 | 30 w 5 d | 744 | 6 | 9.6 | 1.5 | 8.1 | 15.6 | 11.1 | 0.64 | 3.1 |
| 302 | 2 | 39 w 2 d | 2054 | 2 | 8.6 | 6 | 2.6 | 69.8 | 9.9 | 0.94 | 3.3 |
| 306 | 2 | 39 w 2 d | 2054 | 3 | 8.7 | 6.1 | 2.6 | 70.1 | 9.7 | 0.98 | 3.4 |
| 312 | 2 | 39 w 2 d | 2054 | 5 | 7.2 | 5 | 2.2 | 69.4 | 8.1 | 0.68 | 3.1 |
| 359 | 3 | 38 w 4 d | 2362 | 4 | 8.0 | 6.0 | 2.0 | 75.0 | 9.0 | 1.21 | 3.2 |
| 397 | 4 | 39 w 0 d | 2526 | 16 | 5 | 1.3 | 3.7 | 26.0 | 5.7 | 0.29 | 1.9 |
| 413 | 4 | 39 w 0 d | 2526 | 52 | 4.9 | 3.5 | 1.4 | 71.4 | 5.9 | 0.68 | 2.8 |

(Measurement of Unconjugated Bilirubin, Comparison to GOD-POD Method)

Figure 20:
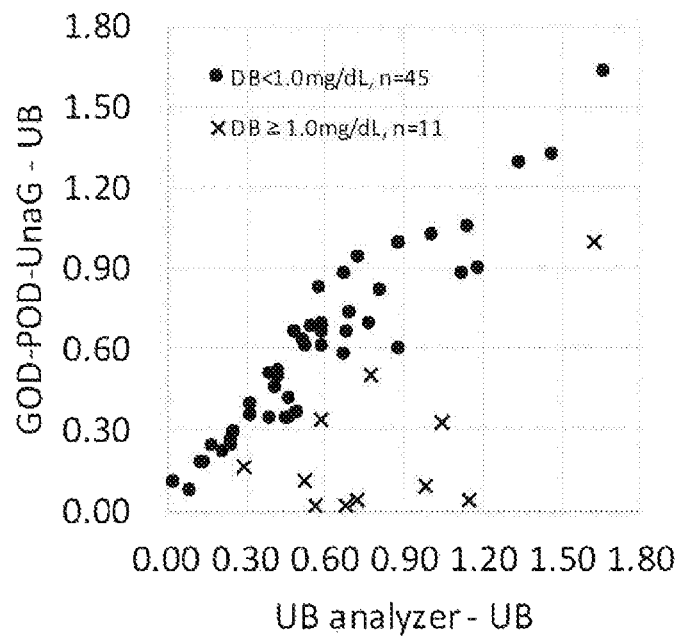
FIG. 20 shows the correlation observed in serum specimens with high DB concentrations in Example 4, between the UB concentrations (UB analyzer UB) measured with a UB analyzer by the conventional measurement method and the UB concentrations (GOD-POD-UnaG-UB) calculated from the iDB concentrations attributable to the GOD-POD-UnaG method, superimposed on FIG. 19.

In the same manner as in Example 2, the 11 serum specimens were subjected to measurement of unbound bilirubin (UB) by the GOD-POD-UnaG method of the present invention. The UB concentrations measured with a UB analyzer by the conventional measurement method (the GOD-POD method) (UB analyzer UB) were compared with the UB concentrations (GOD-POD-UnaG-UB) calculated from the iDB concentrations measured by the GOD-POD-UnaG method of the present invention to see if there was a correlation therebetween. The results are shown in FIG. 20. In FIG. 20, the results from the 11 specimens (plotted with X dots) are superimposed on FIG. 19 that shows the results of Example 3.

As shown in FIG. 20, the plot distribution attributable to this example with high DB concentrations is different from the plot distribution attributable to Example 3 with low DB concentrations. This means that the conventional GOD-POD method tends to give relatively high concentrations.

[Relationship Between iDB/Alb Ratio and UB]

Figure 21:
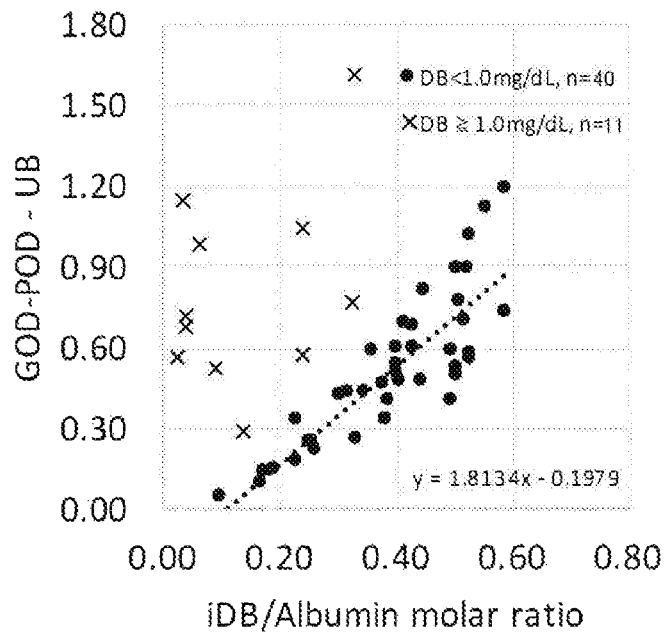
FIG. 21 shows the relationship observed between the iDB/Alb molar ratios and the UB concentrations measured with a UB analyzer by the conventional measurement method, observed in specimens with low DB concentrations in Example 3 and specimens with high DB concentrations in Example 4.
Figure 22:
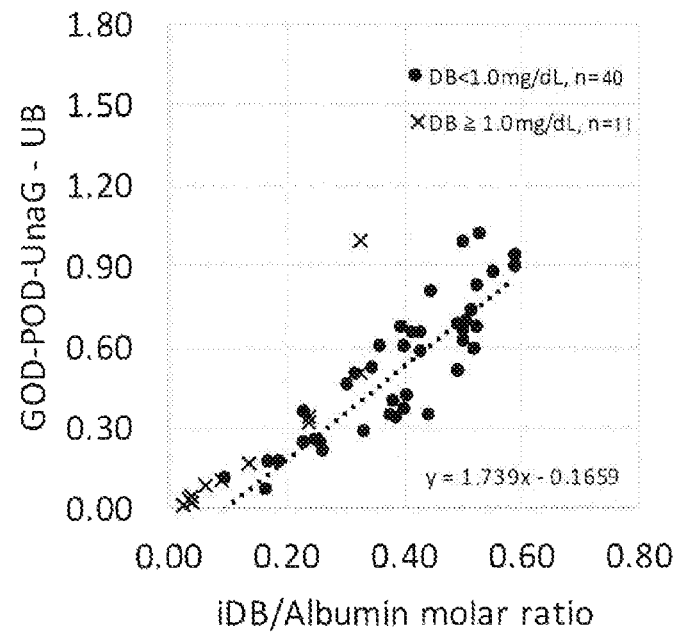
FIG. 22 shows the relationship observed between the iDB/Alb molar ratios and the UB concentrations measured by the GOD-POD-UnaG method of the present invention, observed in specimens with low DB concentrations in Example 3 and specimens with high DB concentrations in Example 4.

The relationship between the iDB/Alb molar ratios and the UB concentrations was evaluated using the specimens with low DB levels (DB<1.0 mg/dL) of Example 3 and the specimens with high DB levels (DB≥1.0 mg/dL) of Example 4. The results are shown in FIGS. 21 and 22. FIG. 21 shows the relationship between the iDB/Alb molar ratios and the UB concentrations measured with a UB analyzer by the conventional measurement method. FIG. 22 shows the relationship between the iDB/Alb molar ratios and the UB concentrations measured by the GOD-POD-UnaG method of the present invention. FIGS. 21 and 22 show specimens with iDB/Alb molar ratios of not higher than 0.6, more specifically, the 40 specimens with low DB levels (plotted with ● dots) and the 11 specimens with high DB levels (plotted with x dots).

As shown in FIG. 21, in the case in which the conventional GOD-POD method was used, the 40 specimens with low DB levels showed a clear correlation ($r=0.849$, $P<0.001$) and the 11 specimens with high DB levels showed a poor correlation ($r=0.375$, $p=0.255$).

On the other hand, as shown in FIG. 22, in the case in which the GOD-POD-UnaG method of the present invention was used, the 40 specimens with low DB levels showed a clear correlation ($r=0.874$, $P<0.001$) and the 11 specimens with high DB levels also showed a clear correlation ($r=0.895$, $p<0.001$).

The preferable embodiments of the present invention are described above. The scope of the present invention is not limited to these embodiments and may be modified in various ways within the purport of the present invention.

The invention claimed is:

1. A method of measuring unbound bilirubin in a blood sample, the method comprising:
   a decomposition step (i) that comprises subjecting a blood sample containing unconjugated bilirubin and conjugated bilirubin to oxidative decomposition reaction in which unbound bilirubin of the unconjugated bilirubin and the conjugated bilirubin receive the oxidative decomposition reaction;
   a decomposition termination step (ii) that comprises terminating the oxidative decomposition reaction to obtain a decomposed sample;
   a contact step (iii) that comprises separately bringing the decomposed sample and a non-reacted sample into contact with a polypeptide, the non-reacted sample being a blood sample not subjected to the oxidative decomposition reaction, the polypeptide having an ability to specifically bind to unconjugated bilirubin and display fluorescence properties; and
   a detection step (iv) that comprises detecting fluorescence attributable to the polypeptide in each of the decomposed sample and the non-reacted sample, and using a difference between the fluorescence attributable to the decomposed sample and the fluorescence attributable to the non-reacted sample to determine a level of the unbound bilirubin.

2. The method of measuring unbound bilirubin according to claim 1, wherein the blood sample is derived from a preterm infant.

3. The method of measuring unbound bilirubin according to claim 1, wherein the blood sample has a serum total bilirubin concentration of not lower than 8 mg/dL.

4. The method of measuring unbound bilirubin according to claim 1, wherein the blood sample has a conjugated bilirubin concentration of not lower than 1 mg/dL.

5. The method of measuring unbound bilirubin according to claim 1, wherein the termination of the oxidative decomposition reaction is carried out by addition of an antioxidant substance.

6. The method of measuring unbound bilirubin according to claim 5, wherein the antioxidant substance is ascorbic acid.

7. The method of measuring unbound bilirubin according to claim 1, wherein the termination of the oxidative decomposition reaction is carried out after a lapse of not shorter than 10 seconds and not longer than 60 seconds from the initiation of the oxidative decomposition reaction in decomposition step (i).

8. The method of measuring unbound bilirubin according to claim 1, wherein the addition of the antioxidant substance is carried out so as to achieve a concentration of the antioxidant substance of not lower than 0.1 wt % in the reaction system in decomposition termination step (ii).

9. The method of measuring unbound bilirubin according to claim 8, wherein in a case in which the antioxidant substance is ascorbic acid, the addition of the ascorbic acid is carried out so as to achieve a concentration of the ascorbic acid of not higher than 32 wt % in the reaction system in decomposition termination step (ii).

10. The method of measuring unbound bilirubin according to claim 9, wherein the ascorbic acid is diluted so as to achieve a concentration of the ascorbic acid of not higher than 0.8 wt % in the reaction system in contact step (iii).

11. The method of measuring unbound bilirubin according to claim 1, wherein a dilution factor of the blood sample in the reaction system in decomposition step (i) is not smaller than 5 and not greater than 120 in terms of serum.

12. The method of measuring unbound bilirubin according to claim 11, wherein
   in decomposition step (i)
   the oxidative decomposition reaction proceeds based on hydrogen peroxide and peroxidase, the hydrogen peroxide is generated from glucose in the presence of glucose oxidase, and
   the reaction system of the oxidative decomposition reaction contains the glucose oxidase and the peroxidase each in an amount of not lower than 0.0128 U and not higher than 0.256 U per 1 μL of serum.

13. The method of measuring unbound bilirubin according to claim 1, wherein the blood sample is a whole blood sample.

14. The method of measuring unbound bilirubin according to claim 13, wherein the level of the unbound bilirubin determined in detection step (iv) is obtained after hematocrit correction.

15. The method of measuring unbound bilirubin according to claim 6, wherein the ascorbic acid is diluted so as to achieve a concentration of the ascorbic acid of not higher than 0.8 wt % in the reaction system in contact step (iii).

* * * * *